(12) United States Patent
Lin et al.

(10) Patent No.: US 7,494,660 B2
(45) Date of Patent: Feb. 24, 2009

(54) HCV NS3-NS4A PROTEASE RESISTANCE MUTANTS

(75) Inventors: Chao Lin, Winchester, MA (US); Kai Lin, Waltham, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 227 days.

(21) Appl. No.: 10/974,558

(22) Filed: Oct. 27, 2004

(65) Prior Publication Data

US 2005/0136400 A1    Jun. 23, 2005

Related U.S. Application Data

(60) Provisional application No. 60/561,662, filed on Apr. 13, 2004, provisional application No. 60/525,222, filed on Nov. 26, 2003, provisional application No. 60/514,740, filed on Oct. 27, 2003.

(51) Int. Cl.
*C12N 7/00*     (2006.01)
*C07H 21/04*    (2006.01)

(52) U.S. Cl. .................................... 424/218.1; 536/23.1
(58) Field of Classification Search .................. None
See application file for complete search history.

(56) References Cited

U.S. PATENT DOCUMENTS

| | | | |
|---|---|---|---|
| 4,835,168 | A | 5/1989 | Paget et al. |
| 5,484,801 | A | 1/1996 | Al-Razzak et al. |
| 5,631,128 | A | 5/1997 | Kozal et al. |
| 5,807,876 | A | 9/1998 | Armistead et al. |
| 5,990,276 | A | 11/1999 | Zhang et al. |
| 6,037,157 | A | 3/2000 | Norbeck et al. |
| 6,054,472 | A | 4/2000 | Armistead et al. |
| 6,127,422 | A | 10/2000 | Colacino et al. |
| 6,162,613 | A | 12/2000 | Su et al. |
| 6,344,465 | B1 | 2/2002 | Armistead et al. |
| 6,489,098 | B1 | 12/2002 | Petropoulos et al. |
| 6,498,178 | B2 | 12/2002 | Stamos et al. |
| 6,541,496 | B1 | 4/2003 | Armistead et al. |
| 6,608,027 | B1 | 8/2003 | Tsantrizos et al. |
| 6,617,130 | B1 | 9/2003 | Bogosian et al. |
| 6,617,156 | B1 | 9/2003 | Doucette-Stamm et al. |

FOREIGN PATENT DOCUMENTS

| | | |
|---|---|---|
| WO | WO-94/14436 A1 | 7/1994 |
| WO | WO-95/07696 A1 | 3/1995 |
| WO | WO-95/09614 A1 | 4/1995 |
| WO | WO-97/40028 A1 | 10/1997 |
| WO | WO-97/43310 A1 | 11/1997 |
| WO | WO-98/11134 A1 | 3/1998 |
| WO | WO-98/17679 A1 | 4/1998 |
| WO | WO-98/40381 A1 | 9/1998 |
| WO | WO-98/46630 A1 | 10/1998 |
| WO | WO-99/07733 A2 | 2/1999 |
| WO | WO-99/07734 A2 | 2/1999 |
| WO | WO-99/50230 A1 | 10/1999 |
| WO | WO-99/64442 A1 | 12/1999 |
| WO | WO-00/09543 | 2/2000 |
| WO | WO-00/09558 A1 | 2/2000 |
| WO | WO-00/56331 A1 | 9/2000 |
| WO | WO-00/59929 A1 | 10/2000 |
| WO | WO-02/08244 A2 | 1/2002 |
| WO | WO-02/18369 A2 | 3/2002 |
| WO | WO-02/068933 A2 | 9/2002 |

OTHER PUBLICATIONS

Lin et al. Antimicrobial Agents and Chemotherapy, 2006, vol. 50, p. 1813-1822.*
Alberti et al., J. Hepatol., 31 Suppl 1:17-24 (1999).
Alter et al., Gastroenterol. Clin. North Am., 23(3):437-455 (1994).
Alter, J. Hepatol., 31 Suppl 1:88-91 (1999).
Alter et al., Semin. Liver Dis., 20(1):17-35 (2000).
Barbato et al., J. Mol. Biol., 289(2):371-384 (1999).
Beyer et al., Proteins, 43(2):82-88 (2001).
Blight et al., Antivir. Ther., 3(Suppl 3):71-81 (1998).
Casbarra et al., Protein Sci., 11:2102-2112 (2002).
Chander et al., Hepatology, 36(5 Suppl 1):S135-S144 (2002).
Chena Nucleosides Nucleotides, 3:421-535 (1994) Not Found.
Choo et al., Science, 244:359-362 (1989).
Clayette et al., Pathol. Biol., 47(5):553-559 (1999).
Davis et al., N. Engl. J. Med., 339(21):1493-1499 (1998).
Davis et al., Semin. Liver Dis., 19 Suppl., 1:103-112 (1999).
De Francesco et al., Antiviral Res., 58(1):1-16 (2003).
De Francesco et al., Curr. Top. Microbiol. Immunol., 242:149-169 (2000).
Dunsdon et al., Bioorg. Med. Chem. Lett., 10(14):1577-1579 (2000).
Han et al., Bioorg. Med. Chem. Lett., 10(8):711-713 (2000).
Iwarson, FEMS Microbiol. Rev., 14(3):201-204 (1994).
Janssen et al., J. Hepatol., 21(2):241-243 (1994).
J. Viral. Hepat., "Global Surveillance and Control of Hepatitis," 6(1):35-47 (1999).
Kao et al., J. Gastroenterol. Hepatol., 15(12):1418-1423 (2000).
Kenny-Walsh, Clin. Liver Dis., 5(4):969-977 (2001).
Kew, FEMS Microbiol. Rev., 14(3):211-219 (1994).
Kim et al., Biochem. Biophys. Res. Commun., 215(1):160-166 (1995).
Koch et al., Virology, 237:78-88 (1997).
Landro et al., Biochemistry, 36(31):9340-9348 (1997).
LaPlante et al., Bioorg. Med. Chem. Lett., 10(20):2271-2274 (2000).
Llinas-Brunet et al., Bioorg. Med. Chem. Lett., 8(13):1713-1718 (1998).
Llinas-Brunet et al., Bioorg. Med. Chem. Lett., 10(20):2267-2270 (2000).
McCoy et al., J. Mol. Biol., 305(5):1099-1110 (2001).
McHutchison et al., Hepatology, 36(5 Suppl 1):S245-S252 (2002).
McHutchinson et al., N. Engl. J. Med., 339(21):1485-1492 (1998).
Moradpour et al., Eur. J. Gastroenterol. Hepatol., 11(11):1199-1202 (1999).

(Continued)

*Primary Examiner*—Stacy B. Chen
*Assistant Examiner*—Agnieszka Boesen
(74) *Attorney, Agent, or Firm*—Marshall, Gerstein & Borun LLP

(57) ABSTRACT

The present invention is directed to mutants of HCV NS3/4A protease. More particularly, the present invention identifies mutant of HCV NS3/4A protease that are resistant to drug treatment.

23 Claims, 13 Drawing Sheets

OTHER PUBLICATIONS

Morrison, Biochim. Biophys. Acta, 185(2):269-286 (1969).
Reddy et al., Hepatology, 33(2):433-438 (2001).
Renault et al., Semin. Liver Dis., 9(4):273-277 (1989).
Rice, Field Virology Book, pp. 931-959 (1996).
Sauder, J. Am. Acad. Dermatol., 43(1 Pt 2):S6-S11 (2000).
Simon et al., Hepatology, 25(2):445-448 (1997).
Steinkuhler et al., Curr. Med. Chem., 8(8):919-932 (2001).
Taliani et al., Anal. Biochem., 240(1):60-67 (1996).
Tazulakhova et al., J. Interferon. Cytokine Res., 21(2):65-73 (2001).
Tsantrizos et al., Angew. Chem. Int. Ed. Engl.,42(12):1356-1360 (2003).
Vorgruggen, Acta Biochim. Pol., 43(1):25-36 (1996).
Wasley et al., Semin. Liver Dis., 20(1):1-16 (2000).
Weiland, FEMS Microbiol. Ev., 14(3):279-288 (1994).
Yao et al., Structure Fold Des., 7(11):1353-1363 (1999).
Younossi et al., Semin. Liver Dis., 19 Suppl 1:95-102 (1999).
Yun et al., Drug Metab. Dispos., 21(3):403-409 (1993).
Bartenschlager et al., J. Virol., 67(7):3835-3844 (1993).
Bartenschlager et al., J. Virol., 69(12):7519-7528 (1995).
Behrens et al., EMBO J., 15(1):12-22 (1996).
Blight et al., Science, 290:1972-1974 (2000).
Chambers et al., Proc. Natl. Acad. Sci. USA, 87:8898-8902 (1990).
Choo et al., Proc. Natl. Acad. Sci. USA, 88:2451-2455 (1991).
Colacino et al., Antimicrob. Agents Chemother., 34(11):2156-2163 (1990).
Di Marco et al., J. Biol. Chem., 275(10):7152-7157 (2000).
Failla et al., J. Virol., 69(3):1769-1777 (1995).
Frese et al., J. Gen. Virol., 82:723-733 (2001).
GenBank CAB46913 Science 285 110-113 (1999).
Grakoui et al., J. Virol., 67(3):1385-1395 (1993).
Grakoui et al., J. Virol., 67(5):2832-2843 (1993).
Grakoui et al., Proc. Natl. Acad. Sci. USA, 90:10583-10587 (1993).
Hijikata et al., Proc. Natl. Acad. Sci. USA, 90:10773-10777 (1993).
Hijikata et al., J. Virol., 67(8):4665-4675 (1993).
Hirsch et al., Clin. Infect. Dis., 37:113-128 (2003).
International Search Report in PCT/US2004/035839 dated Apr. 6, 2005.
Kato et al., Proc. Natl. Acad. Sci. USA, 87:9524-9528 (1990).
Kim et al., Cell, 87:343-355 (1996).
Kolykhalov et al., J. Virol., 74(4):2046-2051 (2000).
Kolykhalov et al., Science, 277:570-574 (1997).
Krieger et al., J. Virol., 75(10):4614-4624 (2001).
Lahm et al., Curr. Drug Targets, 3:281-296 (2002).
Lai et al., Clin. Infect. Dis., 36:687-696 (2003).
Lamarre et al., Nature, 426:186-189 (2003).
Lin et al., J. Biol. Chem., 279(17):17508-17514 (2004).
Lin et al., J. Virol., 68(12):8147-8157 (1994).
Lin et al., J. Virol., 69(7):4373-4380 (1995).
Lin et al., Proc. Natl. Acad. Sci. USA, 92:7622-7626 (1995).
Lohmann et al., J. Virol., 75(3):1437-1449 (2001).
Lohmann et al., Science, 285:110-113 (1999).
Love et al., Cell, 87(2):331-342 (1996).
Markland et al., Antimicrob. Agents Chemother., 44(4):859-866 (2000).
Migliaccio et al., J. Biol. Chem., 278(49):49164-49170 (2003).
Neumann et al., Science, 282:103-107 (1998).
Nguyen et al., Antimicrob. Agents Chemother., 47(11):3525-3530 (2003).
Pause et al., J. Biol. Chem., 278(22):20374-20380 (2003).
Pietschmann et al., J. Virol., 75(3):1252-1264 (2001).
Saito et al., Proc. Natl. Acad. Sci. USA, 87:6547-6549 (1990).
Takamizawa et al., J. Virol., 65(3):1105-1113 (1991).
Tanji et al., J. Virol., 69(3):1575-1581 (1995).
Tomei et al., J. Virol., 67(7):4017-4026 (1993).
Trozzi et al., J. Virol., 77(6):3669-3679 (2003).
Yan et al., Protein Sci., 7:837-847 (1998).

\* cited by examiner

VX-950 (MW. 680)    BILN 2061 (MW. 775)

SEQUENCE LISTING

```
<160> NUMBER OF SEQ ID NOS: 5

<210> SEQ ID NO 1
<211> LENGTH: 2055
<212> TYPE: DNA
<213> ORGANISM: Hepatitis C Virus

<400> SEQUENCE: 1
gcgcctatta cggcctactc ccaacagacg cgaggcctac ttggctgcat catcactagc      60
ctcacaggcc gggacaggaa ccaggtcgag ggggaggtcc aagtggtctc caccgcaaca     120
caatctttcc tggcgacctg cgtcaatggc gtgtgttgga ctgtctatca tggtgccggc     180
tcaaagaccc ttgccggccc aaagggccca atcacccaaa tgtacaccaa tgtggaccag     240
gacctcgtcg gctggcaagc gccccccggg gcgcgttcct tgacaccatg cacctgcggc     300
agctcggacc tttacttggt cacgaggcat gccgatgtca ttccggtgcg ccggcgggc      360 gacagcaggg ggagcctact ctcccccagg cccgtctcct acttgaaggg ctcttcgggc     420
ggtccactgc tctgcccctc ggggcacgct gtgggcatct tcgggctgc  cgtgtgcacc     480 cgaggggttg cgaaggcggt ggactttgta cccgtcgagt ctatggaaac cactatgcgg     540
tccccggtct tcacggacaa ctcgtcccct ccggccgtac cgcagacatt ccaggtggcc     600
catctacacg cccctactgg tagcggcaag agcactaagg tgccggctgc gtatgcagcc     660
```

-continued

```
caagggtata aggtgcttgt cctgaacccg tccgtcgccg ccaccctagg tttcggggcg      720
tatatgtcta aggcacatgg tatcgaccct aacatcagaa ccggggtaag gaccatcacc      780
acgggtgccc ccatcacgta ctccacctat ggcaagtttc ttgccgacgg tggttgctct      840
ggggcgcct atgacatcat aatatgtgat gagtgccact caactgactc gaccactatc      900
ctgggcatcg gcacagtcct ggaccaagcg gagacggctg gagcgcgact cgtcgtgctc      960
gccaccgcta cgcctccggg atcggtcacc gtgccacatc aaacatcga ggaggtggct      1020
ctgtccagca ctggagaaat ccccttttat ggcaaagcca tccccatcga gaccatcaag     1080
gggggaggc acctcatttt ctgccattcc aagaagaaat gtgatgagct cgccgcgaag      1140
ctgtccggcc tcggactcaa tgctgtagca tattaccggg ccttgatgt atccgtcata      1200
ccaactagcg agacgtcat tgtcgtagca acggacgctc taatgacggg ctttaccggc      1260
gatttcgact cagtgatcga ctgcaataca tgtgtcaccc agacagtcga cttcagcctg     1320
gacccgacct tcaccattga cgacgacacc gtgccacaag acgcggtgtc acgtcgcag      1380
cggcgaggca ggactggtag gggcaggatg ggcatttaca ggtttgtgac tccaggagaa     1440
cggccctcgg gcatgttcga ttcctcggtt ctgtgcgagt gctatgacgc gggctgtgct     1500
tggtacgagc tcacgcccgc cgagacctca gttaggttgc gggcttacct aaacacacca     1560
gggttgcccg tctgccagga ccatctggag ttctgggaga cgtctttac aggcctcacc     1620
cacatagacg cccatttctt gtcccagact aagcaggcag agacaacttt cccctacctg     1680
gtagcatacc aggctacggt gtgcgccagg gctcaggctc cacctccatc gtgggaccaa     1740
atgtggaagt gtctcatacg gctaaagcct acgctgcacg gccaacgcc cctgctgtat      1800
aggctgggag ccgttcaaaa cgaggttact accacacacc ccataaccaa atacatcatg     1860
gcatgcatgt cggctgacct ggaggtcgtc acgagcacct gggtgctggt aggcggagtc     1920
ctagcagctc tggccgcgta ttgcctgaca acaggcagcg tggtcattgt gggcaggatc     1980
atcttgtccg gaaagccggc catcattccc gacagggaag tcctttaccg ggagttcgat     2040
gagatggaag agtgc                                                       2055
```

<210> SEQ ID NO 2
<211> LENGTH: 685
<212> TYPE: PRT
<213> ORGANISM: Hepatitis C Virus

<400> SEQUENCE: 2

```
Ala Pro Ile Thr Ala Tyr Ser Gln Gln Thr Arg Gly Leu Leu Gly Cys
1               5                   10                  15

Ile Ile Thr Ser Leu Thr Gly Arg Asp Arg Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Tyr His Gly Ala Gly Ser Lys Thr Leu
    50                  55                  60

Ala Gly Pro Lys Gly Pro Ile Thr Gln Met Tyr Thr Asn Val Asp Gln
65                  70                  75                  80

Asp Leu Val Gly Trp Gln Ala Pro Pro Gly Ala Arg Ser Leu Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
        115                 120                 125
```

```
Pro Arg Pro Val Ser Tyr Leu Lys Gly Ser Gly Gly Pro Leu Leu
    130                 135                 140

Cys Pro Ser Gly His Ala Val Gly Ile Phe Arg Ala Val Cys Thr
145                 150                 155                 160

Arg Gly Val Ala Lys Ala Val Asp Phe Val Pro Val Glu Ser Met Glu
                165                 170                 175

Thr Thr Met Arg Ser Pro Val Phe Thr Asp Asn Ser Ser Pro Pro Ala
            180                 185                 190

Val Pro Gln Thr Phe Gln Val Ala His Leu His Ala Pro Thr Gly Ser
        195                 200                 205

Gly Lys Ser Thr Lys Val Pro Ala Ala Tyr Ala Ala Gln Gly Tyr Lys
    210                 215                 220

Val Leu Val Leu Asn Pro Ser Val Ala Ala Thr Leu Gly Phe Gly Ala
225                 230                 235                 240

Tyr Met Ser Lys Ala His Gly Ile Asp Pro Asn Ile Arg Thr Gly Val
                245                 250                 255

Arg Thr Ile Thr Thr Gly Ala Pro Ile Thr Tyr Ser Thr Tyr Gly Lys
            260                 265                 270

Phe Leu Ala Asp Gly Gly Cys Ser Gly Gly Ala Tyr Asp Ile Ile Ile
        275                 280                 285

Cys Asp Glu Cys His Ser Thr Asp Ser Thr Thr Ile Leu Gly Ile Gly
290                 295                 300

Thr Val Leu Asp Gln Ala Glu Thr Ala Gly Ala Arg Leu Val Val Leu
305                 310                 315                 320

Ala Thr Ala Thr Pro Pro Gly Ser Val Thr Val Pro His Pro Asn Ile
                325                 330                 335

Glu Glu Val Ala Leu Ser Ser Thr Gly Glu Ile Pro Phe Tyr Gly Lys
            340                 345                 350

Ala Ile Pro Ile Glu Thr Ile Lys Gly Gly Arg His Leu Ile Phe Cys
        355                 360                 365

His Ser Lys Lys Lys Cys Asp Glu Leu Ala Ala Lys Leu Ser Gly Leu
    370                 375                 380

Gly Leu Asn Ala Val Ala Tyr Tyr Arg Gly Leu Asp Val Ser Val Ile
385                 390                 395                 400

Pro Thr Ser Gly Asp Val Ile Val Val Ala Thr Asp Ala Leu Met Thr
                405                 410                 415

Gly Phe Thr Gly Asp Phe Asp Ser Val Ile Asp Cys Asn Thr Cys Val
            420                 425                 430

Thr Gln Thr Val Asp Phe Ser Leu Asp Pro Thr Phe Thr Ile Glu Thr
        435                 440                 445

Thr Thr Val Pro Gln Asp Ala Val Ser Arg Ser Gln Arg Arg Gly Arg
    450                 455                 460

Thr Gly Arg Gly Arg Met Gly Ile Tyr Arg Phe Val Thr Pro Gly Glu
465                 470                 475                 480

Arg Pro Ser Gly Met Phe Asp Ser Ser Val Leu Cys Glu Cys Tyr Asp
                485                 490                 495

Ala Gly Cys Ala Trp Tyr Glu Leu Thr Pro Ala Glu Thr Ser Val Arg
            500                 505                 510

Leu Arg Ala Tyr Leu Asn Thr Pro Gly Leu Pro Val Cys Gln Asp His
        515                 520                 525

Leu Glu Phe Trp Glu Ser Val Phe Thr Gly Leu Thr His Ile Asp Ala
    530                 535                 540
```

-continued

```
His Phe Leu Ser Gln Thr Lys Gln Ala Gly Asp Asn Phe Pro Tyr Leu
545                 550                 555                 560

Val Ala Tyr Gln Ala Thr Val Cys Ala Arg Ala Gln Ala Pro Pro Pro
                565                 570                 575

Ser Trp Asp Gln Met Trp Lys Cys Leu Ile Arg Leu Lys Pro Thr Leu
            580                 585                 590

His Gly Pro Thr Pro Leu Leu Tyr Arg Leu Gly Ala Val Gln Asn Glu
        595                 600                 605

Val Thr Thr Thr His Pro Ile Thr Lys Tyr Ile Met Ala Cys Met Ser
610                 615                 620

Ala Asp Leu Glu Val Val Thr Ser Thr Trp Val Leu Val Gly Gly Val
625                 630                 635                 640

Leu Ala Ala Leu Ala Ala Tyr Cys Leu Thr Thr Gly Ser Val Val Ile
                645                 650                 655

Val Gly Arg Ile Ile Leu Ser Gly Lys Pro Ala Ile Ile Pro Asp Arg
            660                 665                 670

Glu Val Leu Tyr Arg Glu Phe Asp Glu Met Glu Glu Cys
        675                 680                 685

<210> SEQ ID NO 3
<211> LENGTH: 18
<212> TYPE: DNA
<213> ORGANISM: Artificial sequence
<220> FEATURE:
<223> OTHER INFORMATION: Synthetic primer

<400> SEQUENCE: 3
ccttctatcg ccttcttg                                                  18

<210> SEQ ID NO 4
<211> LENGTH: 17
<212> TYPE: DNA
<213> ORGANISM: Artificial sequence
<220> FEATURE:
<223> OTHER INFORMATION: Synthetic primer

<400> SEQUENCE: 4
cttgatggtc tcgatgg                                                   17

<210> SEQ ID NO 5
<211> LENGTH: 16
<212> TYPE: PRT
<213> ORGANISM: Artificial sequence
<220> FEATURE:
<223> OTHER INFORMATION: Synthetic peptide

<400> SEQUENCE: 5

Lys Lys Gly Ser Val Val Ile Val Gly Arg Ile Val Leu Ser Gly Lys
1               5                   10                  15
```

HCV NS3-NS4A PROTEASE RESISTANCE MUTANTS

The present application claims the benefit of priority of U.S. Provisional Application No. 60/514,740 filed Oct. 27, 2003; U.S. Provisional Application No. 60/525,222 filed Nov. 26, 2003; U.S. Provisional Application No. 60/561,662 filed Apr. 13, 2004. The entire text of each of the foregoing applications is specifically incorporated herein by reference in its entirety.

BACKGROUND

1. Field of the Invention

The present invention relates to resistance mutants of Hepatitis C virus NS3/4A protease.

2. Background of the Related Art

Infection by hepatitis C virus ("HCV") is a compelling human medical problem. HCV is recognized as the causative agent for most cases of non-A, non-B hepatitis, with an estimated human sero-prevalence of 3% globally [A. Alberti et al., "Natural History of Hepatitis C," J. Hepatology, 31., (Suppl. 1), pp. 17-24 (1999)]. Nearly four million individuals may be infected in the United States alone [M. J. Alter et al., "The Epidemiology of Viral Hepatitis in the United States, Gastroenterol. Clin. North Am., 23, pp. 437-455 (1994); M. J. Alter "Hepatitis C Virus Infection in the United States," J. Hepatology, 31., (Suppl. 1), pp. 88-91 (1999)].

Upon first exposure to HCV only about 20% of infected individuals develop acute clinical hepatitis while others appear not to develop significant outward symptoms of infection. In almost 70% of instances, however, the virus establishes a chronic infection that persists for decades [S. Iwarson, "The Natural Course of Chronic Hepatitis," FEMS Microbiology Reviews, 14, pp. 201-204 (1994); D. Lavanchy, "Global Surveillance and Control of Hepatitis C," J. Viral Hepatitis, 6, pp. 35-47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", FEMS Microbiology Reviews, 14, pp. 211-220 (1994); I. Saito et. al., "Hepatitis C Virus Infection is Associated with the Development of Hepatocellular Carcinoma," Proc. Natl. Acad. Sci. USA, 87, pp. 6547-6549 (1990)]. Unfortunately, there are no broadly effective treatments for the debilitating progression of chronic HCV.

The HCV genome encodes a polyprotein of 3010-3033 amino acids [Q. L. Choo, et. al., "Genetic Organization and Diversity of the Hepatitis C Virus." Proc. Natl. Acad. Sci. USA, 88, pp. 2451-2455 (1991); N. Kato et al., "Molecular Cloning of the Human Hepatitis C Virus Genome From Japanese Patients with Non-A, Non-B Hepatitis," Proc. Natl. Acad. Sci. USA, 87, pp. 9524-9528 (1990); A. Takamizawa et. al., "Structure and Organization of the Hepatitis C Virus Genome Isolated From Human Carriers," J. Virol., 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et. al., "Nonstructural Protein 3 of the Hepatitis C Virus Encodes a Serine-Type Proteinase Required for Cleavage at the NS3/4 and NS4/5 Junctions," J. Virol., 67, pp. 3835-3844 (1993); A. Grakoui et. al., "Characterization of the Hepatitis C Virus-Encoded Serine Proteinase: Determination of Proteinase-Dependent Polyprotein Cleavage Sites," J. Virol., 67, pp. 2832-2843 (1993); A. Grakoui et. al., "Expression and Identification of Hepatitis C Virus Polyprotein Cleavage Products," J. Virol., 67, pp. 1385-1395 (1993); L. Tomei et. al., "NS3 is a serine protease required for processing of hepatitis C virus polyprotein", J. Virol., 67, pp. 4017-4026 (1993)].

The HCV NS protein 3 (NS3) contains a serine protease activity that processes viral polyprotein to generate the majority of the viral enzymes, and is essential for viral replication and infectivity. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", J. Virol., 68, pp. 8147-8157 (1994)]. Substitutions of the catalytic triad of the HCV NS3 serine protease resulted in loss of viral replication and infectivity in chimpanzees [A. A. Kolykhalov et al., "Hepatitis C virus-encoded enzymatic activities and conserved RNA elements in the 3' nontranslated region are essential for virus replication in vivo", J. Virol., 74: 2046-2051]. It is known that mutations in the yellow fever virus NS3 protease decrease viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", Proc. Natl. Acad. Sci. USA, 87, pp. 8898-8902 (1990)].

The HCV NS3serine protease and its associated cofactor, NS4A, processes the viral non-structural protein region into individual non-structural proteins, including all of the viral enzymes [C. Failla, et al., "An amino-terminal domain of the hepatitis C virus NS3 protease is essential for interaction with NS4A", J. Virol. 69, pp. 1769-1777; Y. Tanji et al., "Hepatitits C virus-encoded nonstructural protein NS4A has versatile functions in viral protein processing", J. Virol. 69, pp. 1575-1581; C. Lin et al., "A central region in the hepatitis C virus NS4A protein allows formation of an active NS3-NS4A serine proteinase complex in vivo and in vitro", J. Virol. 69, pp. 4373-4380], and is essential for viral replication. This processing appears to be analogous to that carried out by the human immunodeficiency virus aspartyl protease, which is also involved in processing of viral proteins. HIV protease inhibitors, which inhibit viral protein processing, are potent antiviral agents in man, indicating that interrupting this stage of the viral life cycle results in therapeutically active agents. Consequently it is an attractive target for drug discovery.

Several potential HCV protease inhibitors have been described in the prior art [PCT publication Nos. WO 02/18369, WO 02/08244, WO 00/09558, WO 00/09543, WO 99/64442, WO 99/07733, WO 99/07734, WO 99/50230, WO 98/46630, WO 98/17679 and WO 97/43310, U.S. Pat. No. 5,990,276, M. Llinas-Brunet et al., Bioorg. Med. Chem. Lett., 8, pp. 1713-18 (1998); W. Han et al., Bioorg. Med. Chem. Lett., 10, 711-13 (2000); R. Dunsdon et al., Bioorg. Med. Chem. Lett., 10, pp. 1571-79 (2000); M. Llinas-Brunet et al., Bioorg. Med. Chem. Lett., 10, pp. 2267-70 (2000); and S. LaPlante et al., Bioorg. Med. Chem. Lett., 10, pp. 2271-74 (2000)]. It is not known however whether these compounds would have the appropriate profiles to be acceptable drugs. Furthermore, it is possible that the HCV protease may become resistant to an otherwise acceptable drug.

Therefore, the current understanding of HCV has not led to any satisfactory anti-HCV agents or treatments. The only established therapy for HCV disease is interferon alpha-based treatment. However, interferons alpha have significant side effects [M. A. Walker et al., "Hepatitis C Virus: An Overview of Current Approaches and Progess," DDT, 4, pp. 518-29 (1999); D. Moradpour et al., "Current and Evolving Therapies for Hepatitis C," Eur. J. Gastroenterol. Hepatol., 11, pp. 1199-1202 (1999); H. L. A. Janssen et al. "Suicide Associated with Alfa-Interferon Therapy for Chronic Viral Hepatitis," J. Hepatol., 21, pp. 241-243 (1994); P. F. Renault et al., "Side Effects of Alpha Interferon," Seminars in Liver Disease, 9, pp. 273-277. (1989)] and induce long term remission in only a fraction (~25%) of cases [O. Weiland, "Interferon Therapy in Chronic Hepatitis C Virus Infection", FEMS Microbiol. Rev., 14, pp. 279-288 (1994)]. The current standard of care, pegylated interferon alpha in combination with ribavirin, has roughly 40-50% sustained viral response (SVR) for patients infected with genotype 1, which counts for 70% of chronic hepatitis C patients in developed countries, and 80% SVR in genotype 2 or 3 HCV-infected patients [J. G. McHutchison, et al., N. Engl. J. Med., 339: 1485-1492 (1998); G. L. Davis et al., N. Engl. J. Med., 339: 1493-1499 (1998)]. Moreover, the prospects for effective anti-HCV vaccines remain uncertain.

Thus, there is a need for more effective anti-HCV therapies, particularly compounds that inhibit HCV NS3 protease. Such compounds may be useful as antiviral agents, particularly as anti-HCV agents. An understanding of HCV resistance mutants would further progress towards effective HCV treatments.

SUMMARY OF THE INVENTION

The present invention relates to resistance mutants of Hepatitis C virus NS3/4A protease.

Thus, in certain aspects the invention involves isolated HCV polynucleotides that encode mutant HCV NS3/4A proteases or a biologically active analogs or fragments thereof wherein the codon that corresponds to codon 156 of the wild-type polynucleotide and/or the codon that corresponds to codon 168 of the wild-type polynucleotide is mutated such that it does not encode an alanine at 156 and/or aspartic acid at 168. Exemplary such mutations are described herein throughout an include polynucleotides in which the codon that corresponds to 156 of the wild-type polynucleotide encodes a serine, valine or threonine. Other exemplary embodiments include polynucleotides in which the codon of the polynucleotide that corresponds to codon 168 of the wild-type polynucleotide encodes an aspartic acid, glutamic acid, an alanine, a glycine, or a tyrosine. Any combinations of the mutations at codon 156 and 168 are specifically contemplated. The wild-type HCV NS3/4A protease is well known to those of skill in the art. It is encoded by a polynucleotide sequence of SEQ ID NO:1. That polynucleotide sequence encodes an amino acid sequence of SEQ ID NO:2.

Also contemplated herein are the polypeptides or biologically active fragments thereof that are encoded by the polynucleotides described herein. Further the invention encompasses vectors that comprise, host cells that have been transformed or transfected with such polynucleotides and cell lines that comprise such polynucleotides. Methods and compositions for making such vectors, transforming host cells and preparing cell lines are routine and conventional techniques known to those of skill in the art. Isolated HCV variants that comprise the mutant polynucleotides or proteins described herein also are part of the present invention.

Compositions comprising the polynucleotides or proteins either alone or in combination with other compositions and components also are contemplated herein.

The invention teaches method for detecting the presence of drug-resistant HCV in a biological sample comprising detecting the presence of a polynucleotide described herein. Typically, such methods comprise obtaining or isolating the polynucleotide from the sample; determining the sequence of the polynucleotide; and assessing whether a resistance-associated mutation, such as one or more of the mutations described herein (e.g., one that encodes serine, valine, or a threonine at a residue that corresponds to residue 156 and/or encodes a glutamic acid, valine, alanine, glycine, or tyrosine at a residue that corresponds to residue 168 of the wild-type HCV NS3/4A protease) is present in the polynucleotide.

Also contemplated is a methods of determining or diagnosing whether an HCV infection in a patient is drug-resistant comprising collecting a biological sample from the HCV infected patient; and evaluating whether the plasma sample contains nucleic acid encoding a mutant HCV NS3/4A protease, wherein the presence of the mutant HCV NS3/4A protease is indicative of the patient having a drug-resistant HCV infection.

Other aspects contemplate methods of evaluating whether a HCV-infected patient has a decreased sensitivity or susceptibility to VX-950 comprising evaluating whether the patient has a Hepatitis C virus NS3/4A protease DNA having a mutation at the codon that encodes residue 156 of wild-type Hepatitis C virus NS3/4A protease.

Still further aspects are directed to methods for evaluating whether a HCV-infected patient has a decreased sensitivity or susceptibility to a protease inhibitor comprising evaluating whether the patient has a Hepatitis C virus NS3/4A protease DNA having a mutation at the codon that encodes residue 156 of wild-type Hepatitis C virus NS3/4A protease.

The invention further contemplates methods for evaluating a candidate or potential HCV inhibitor comprising introducing a vector comprising a polynucleotide of the invention and indicator gene encoding an indicator into a host cell; culturing the host cell; and measuring the indicator in the presence of inhibitor and in the absence of inhibitor.

Other methods assay compounds for activity against HCV by providing a mutant protease described herein and a protease substrate; contacting the protease with a candidate or potential inhibitor in the presence of the substrate; and evaluating or measuring the inhibition of proteolytic activity of the protease.

Other aspects provide methods of identifying a compound as an inhibitor of a drug-resistant protease described herein by assaying the activity of such protease in the absence of the compound; assaying the activity of the protease in the presence of compound; comparing the results from the assay performed in the presence and absence of the compound, wherein any decrease in protease activity as a result of the presence of the compound indicates that the compound is an inhibitor of the protease.

Methods of identifying compounds that are able to rescue the activity of VX-950, wherein a NS3/4A protease has become resistant to VX-950 also are taught in which the resistant protease is contacted with the compound; and the ability of the VX-950 to inhibit the activity of the protease is assessed in the presence of that compound.

The present invention takes advantage of the fact that the three-dimensional structure of NS3/4A protease has been resolved (see e.g., WO 98/11134). Using such techniques and the teachings of the present invention a three dimensional model of the resistant protease of the invention is obtained; compounds are designed or selected to interact with the three-dimensional structure of the mutant protease and the ability of the compound to bind to or interact with the protease is evaluated (e.g., through molecular modeling). Exemplary three dimensional models are based on the x-ray crystal structure (FIG. 1 and FIG. 2) of NS3/4A protease. Such models may be obtained through computer-implemented methods or through x-ray crystallography. Such evaluations may be compared with evaluations determined from wild-type protease.

The compound may be one identified from a combinatorial chemical library or prepared through rational drug design. In exemplary embodiments, the compound is a compound prepared through rational drug design and derived from the structure of VX-950. In exemplary embodiments, the identified compound is formulated into a composition comprising the compound and a pharmaceutically acceptable carrier, adjuvant or vehicle. Preferably the composition contains the compound in an amount effective to inhibit NS3/4A serine protease. Even more preferably the composition is formulated for administration to a patient. The compositions also may comprise an additional agent selected from an immunomodulatory agent; an antiviral agent; a second inhibitor of HCV protease; an inhibitor of another target in the HCV life cycle; a cytochrome P-450 inhibitor; or combinations thereof.

Other methods of the invention contemplated inhibiting the activity of a Hepatitis C NS3/4A protease comprising the step of contacting the serine protease with such a compound or composition. Further aspects contemplate methods of treating an HCV infection in a patient comprising the step of administering to the patient such a compound of composition.

Still additional aspects contemplate methods of treating or reducing an HCV infection in a patient comprising determining whether the patient has an HCV infection that is resistant to therapy using a method described herein that relies on detection of mutations described and treating the patient with a composition or therapy directed at the treatment of drug-resistant HCV.

Other additional aspects teach methods of eliminating or reducing HCV contamination of a biological sample or medical or laboratory equipment, comprising the step of contacting the biological sample or medical or laboratory equipment with a compound identified as described herein. In still other embodiments, the biological sample or medical or laboratory equipment is contaminated with a drug-resistant strain of HCV as determined according to the methods of determination described herein.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

DESCRIPTION OF THE PREFERRED EMBODIMENTS

Figure 1:
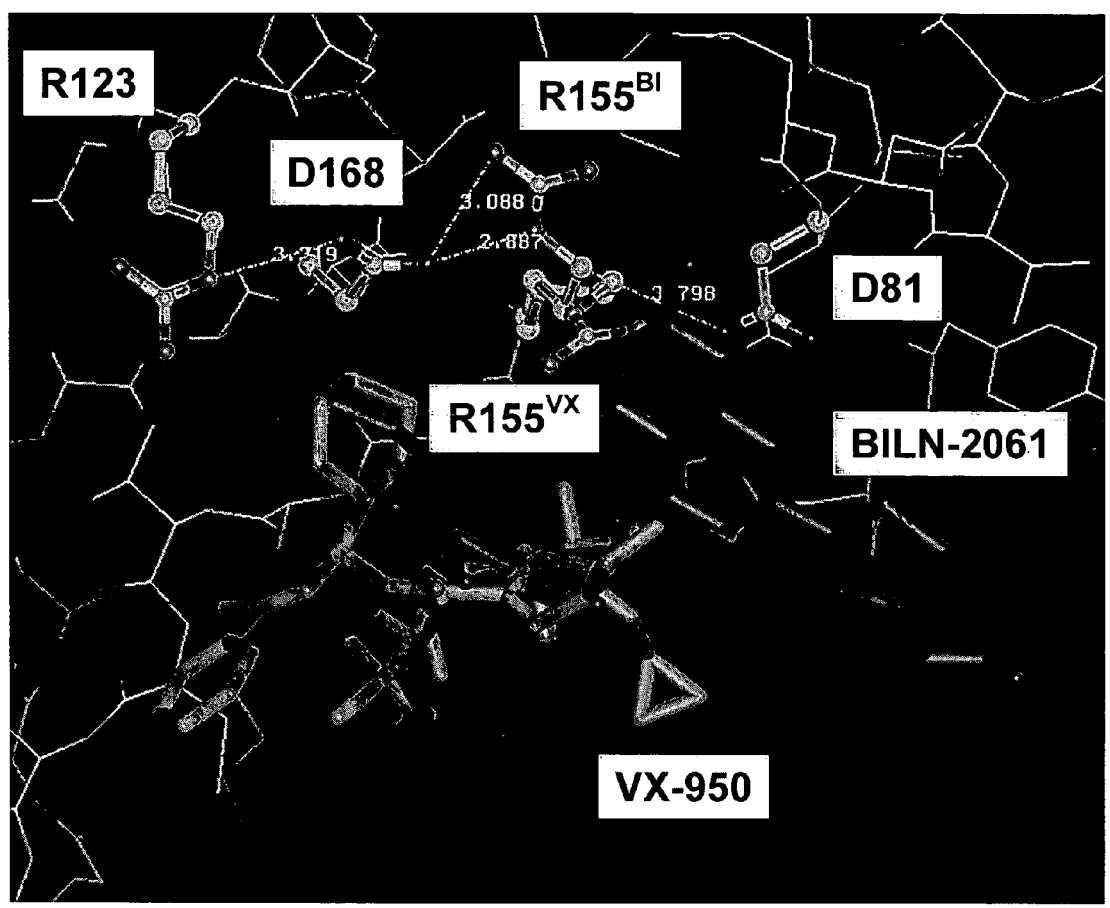
FIG. 1: X-ray Structures of the two HCV NS3 protease-protease inhibitor (PI) complexes of BILN 2061 and VX-950. Two co-complex structures were solved and superimposed (VX-950 in blue and BILN 2061 in red). Three residues shown in ball-and-stick (R123, R155 and D168) form salt bridges in the BILN 2061 structure, but not in the VX-950 structure. Removal of negative charge at D168 results in lack of restriction of R155 and consequent loss of stacking with the large P2 of BILN 2061 and increase in the cost of desolvation. R155 is not restricted by D168 in the VX-950 structure and the D168V mutation does not affect its binding.
Figure 2:
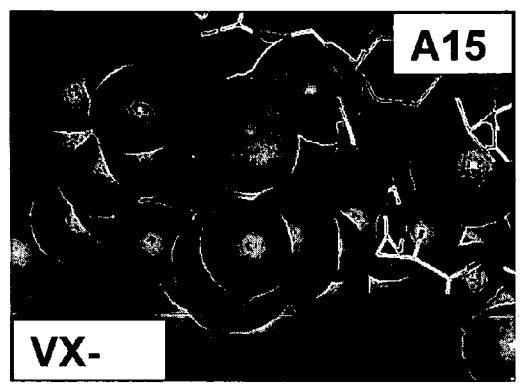
FIG. 2: A156S mutation causes a loss of binding due to steric clash with VX-950, but not with BILN 2061. X-ray structures of VX-950 (top-left, in blue) or BILN 2061 (bottom-left, in red) with wild-type A156 highlighted in yellow. Models of A156S mutation (in NS3 serine protease was sequenced either directly or after being sub-cloned into the TA vector. (B) Titration of VX-950 against the series A (VX-950-resistant) (filled rectangle) or the series C (double-resistant) (open rectangle) replicon cells at day 52 by VX-950 was shown. HCV RNA level was determined after a 48-h incubation with VX-950. (C) Titration of BILN 2061 against the series A (VX-950-resistant) (filled triangle) or the series C (double-resistant) (open triangle) replicon cells at day 52 by BILN 2061 was shown HCV RNA level was determined after a 48-h incubation with BILN 2061.
Figure 2:
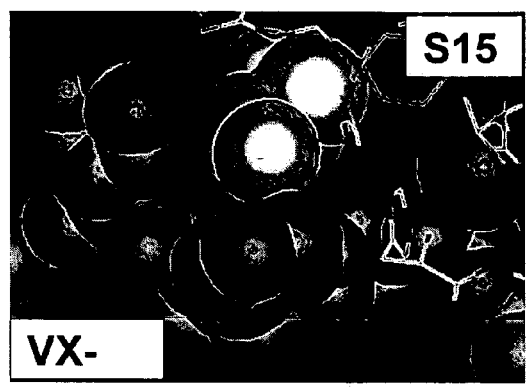
Figure 2:
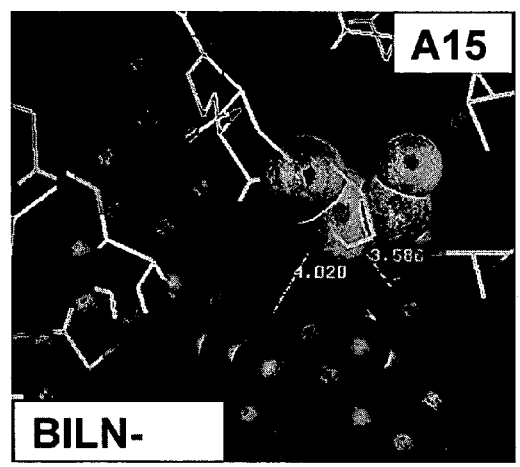
Figure 2:
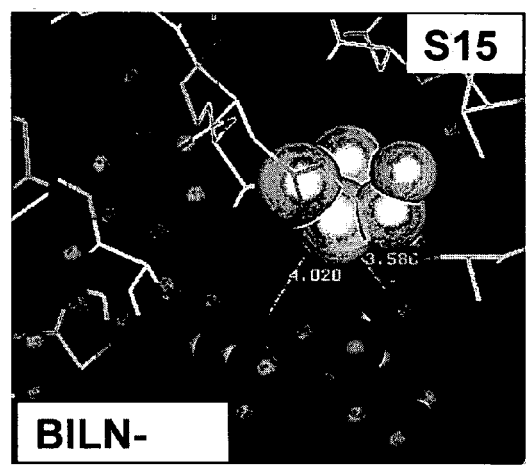
Figure 3:
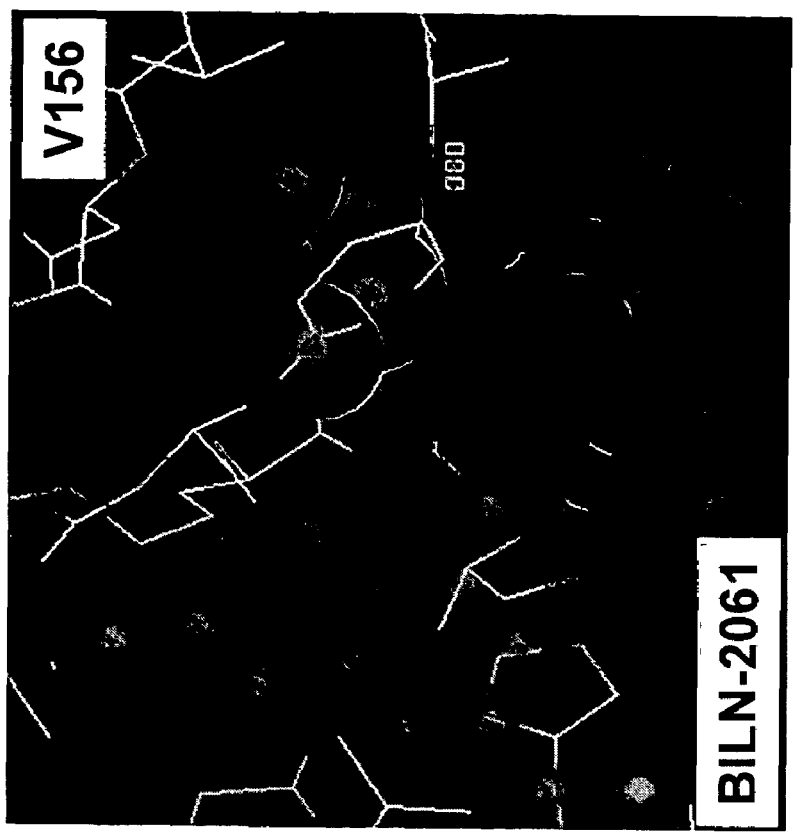
Figure 3:
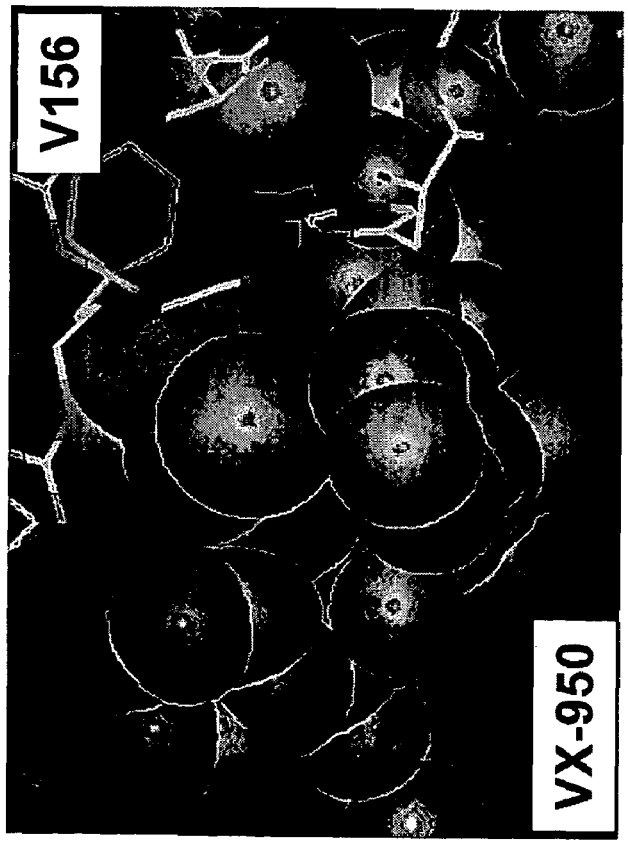

It has been determined by the present inventors that HCV strains undergo particular mutations in the presence of certain therapeutic compounds which renders the HCV strains resistant to the therapeutic potential of those compounds. In particular embodiments, it has been determined that Hepatitis C virus NS3/4A protease is mutated in these HCV resistance mutants such that the mutants are rendered resistant to protease inhibitor compounds. These discoveries may be exploited in the design of therapies for the treatment of HCV infection.

In specific embodiments, it has been determined that amino acid residue 156 of wild-type HCV NS3/4A (the sequence of which is provided as SEQ ID NO:2) is susceptible to mutation. The mutation of this residue leads to resistance of the HCV to therapeutic intervention by protease inhibitors. In one embodiment, it has been shown that the wild-type codon 156, which in the wild-type HCV NS3/4A encodes alanine is mutated to a codon which encodes serine at that relative position in the HCV NS3/4A polypeptide. In another embodiment, the codon is mutated to a codon which encodes valine at that relative position in the HCV NS3/4A polypeptide. In yet another embodiment, threonine is encoded at that relative position in HCV NS3/4A.

In view of the above findings, the invention provides a HCV DNA encoding a HCV NS3/4A protease (or fragment or analog thereof) wherein codon 156 of the DNA encodes a serine. Another embodiment of this invention provides a HCV DNA encoding a HCV NS3/4A protease (or fragment or analog thereof) wherein codon 156 of the DNA encodes a valine. Still a further embodiment provides a HCV DNA encoding a HCV NS3/4A protease (or fragment or analog thereof) wherein codon 156 of the DNA encodes a threonine.

In still further embodiments, it has been determined that in certain embodiments, the codon at 156 is one which encodes valine, serine or threonine at residue 156 which is normally an alanine residue in native/wild-type HCV NS3/4A, and there is a further mutation in which the codon at residue 168 of native/wild-type HCV NS3/4A, which is normally an aspartic acid residue is mutated to a valine, alanine, a glycine or a tyrosine residue. While in certain embodiments, it is contemplated that the mutant HCV NS3/4A protease would possess mutations at both the 156 and 168 positions, it is contemplated that the mutants contain the single mutations also are part of the present invention.

Specific aspects of the invention include HCV DNA encoding a HCV NS3/4A protease (or fragment or analog thereof) wherein codon 156 of the DNA encodes a valine or a threonine and codon 168 encodes an aspartic acid or glutamic acid. Another embodiment of this invention provides a HCV DNA encoding a HCV NS3/4A protease (or fragment or analog thereof) wherein codon 168 of the DNA encodes a valine. Another embodiment of this invention provides a HCV DNA encoding a HCV NS3/4A protease or (or fragment or analog thereof) wherein codon 168 of the DNA encodes an alanine, a glycine, or a tyrosine.

The numbering system for the DNA of this invention is in accordance with the sequence SEQ ID NO. 1. DNA according to this invention may be derived from SEQ ID NO. 1. The DNA may be derived by solid phase synthesis or through recombinant means. In specific embodiments, site-directed mutagenesis of the sequence of SEQ ID NO:2 is particularly contemplated in order to generate one or other of the mutants described herein.

It should be recognized that protein mutations may be complete (i.e., all or about all of the protein is converted to the mutant protein), partial, or absent (i.e., no or about no mutation). Therefore, a composition or method of this invention may comprise a mixture of wild-type and mutated protein.

According to another embodiment of this invention is provided a HCV NS3/4A protease protein (or fragment or analog thereof) comprising amino acid 156 of the protease, wherein amino acid 156 is serine.

Another embodiment of this invention provides a HCV NS3/4A protease protein (or fragment or analog thereof) comprising amino acid 156 of the protease, wherein amino acid 156 is valine.

Another embodiment of this invention provides a HCV NS3/4A protease protein (or fragment or analog thereof) comprising amino acid 156 of the protease, wherein amino acid 156 is threonine.

Another embodiment of this invention provides a HCV NS3/4A protease protein (or fragment or analog thereof) comprising amino acid 156 of the protease, wherein amino acid 156 is valine or threonine and amino acid 168 is aspartic acid or glutamic acid.

Another embodiment of this invention provides an isolated HCV NS3/4A protease protein (or fragment or analog thereof) comprising amino acid 156 of the protease, wherein amino acid 168 is valine.

Another embodiment of this invention provides a HCV NS3/4A protease protein (or fragment or analog thereof) comprising amino acid 156 of the protease, wherein amino acid 168 is alanine, glycine, or tyrosine.

The DNA and the proteins according to this invention may be modified using routine techniques. For example, the DNA may comprise a modification for attaching the DNA to a solid support. The proteins may comprise a covalently-linked marker compound.

The DNA or proteins according to this invention may be in computer readable form, including, but not limited to, on computer readable carriers and/or computer readable databases (see, e.g., WO 98/11134).

For certain uses, the DNA according to this invention may be inserted into a vector. Any suitable vector would be included within the scope of this invention. Suitable vectors are known in the art. One embodiment provides an expression vector. Another embodiment provides a viral vector. A vector may be a cloning tool or may additionally comprise regulatory sequences such a promoter, enhancers and terminators or polyadenylation signals.

Accordingly, this invention also provides a vector comprising a HCV NS3/4A protease DNA (or fragment or analog thereof), wherein:

codon 156 of the DNA encodes a serine;
codon 156 of the DNA encodes a valine;
codon 156 of the DNA encodes a threonine;
codon 156 of the DNA encodes a valine or a threonine and codon 168 encodes an aspartic acid or glutamic acid;
codon 168 of the DNA encodes a valine;
codon 168 of the DNA encodes an alanine;
codon 168 of the DNA encodes a glycine; and/or codon 168 of the DNA encodes a tyrosine.

Another embodiment provides an expression vector. Another embodiment provides a viral vector. A vector may be a cloning tool or may additionally comprise regulatory sequences such a promoters, enhancers and terminators or polyadenylation signals. These vectors may be used in any appropriate host cell. Host cells are known in the art.

Accordingly, this invention also provides a host cell comprising NS3/4A protease DNA wherein codon 156 of the DNA encodes a serine; codon 156 of the DNA encodes a valine; codon 156 of the DNA encodes a threonine; codon 156 of the DNA encodes a valine or a threonine and codon 168 encodes an aspartic acid or glutamic acid; codon 168 of the DNA encodes a valine; codon 168 of the DNA encodes an alanine; codon 168 of the DNA encodes a glycine; and/or codon 168 of the DNA encodes a tyrosine. Expression of the DNA would provide a host cell comprising a protease having an A156 to serine mutation; an A156 to valine mutation; an A156 to threonine mutation; an A156 to valine or threonine and a D168 to glutamic acid mutation; a D168 to valine mutation; D168 to alanine mutation; a D168 to glycine mutation; and/or a D168 to tyrosine mutation. Also provided are cell lines comprising DNA or proteins according to this invention.

The invention also provides a HCV variant comprising a DNA according to this invention or a protein according to this invention and compositions comprising the DNA and proteins.

HCV variants, as well as the DNA and/or proteins according to this invention may be useful in drug discovery as well as in monitoring appropriate HCV therapies.

Accordingly, another embodiment of this invention provides a method detecting the presence of HCV in a biological sample comprising detecting the presence of a DNA according to this invention. These methods may comprise the steps of obtaining (or extracting) a DNA; b) determining the sequence of the DNA; c) determining or inferring whether in the DNA, codon 156 encodes a serine, whether codon 156 encodes a valine, whether codon 156 of the polynucleotide encodes a threonine, whether codon 156 encodes a valine or a threonine and codon 168 encodes an aspartic acid or glutamic acid, whether codon 168 encodes a valine, or whether codon 168 encodes an alanine, a glycine, or a tyrosine. In certain embodiments, the biological sample containing the HCV is derived from a mammal that has been infected with HCV. Detection of the presence of such a DNA may be used diagnostically to guide the practitioner that the individual is one in whom the HCV infection will likely be resistant or otherwise refractory to treatment by protease inhibitors. Given such guidance, the skilled artisan may modify the therapy of the subject having such an infection, but for example increasing the dose of the therapy of providing additional therapies using agents to which the HCV strain infecting the subject is non-resistant.

Methods of this invention may require certain quantities of DNA to be obtained. As would be recognized by skilled practitioners, the DNA would be obtained and then amplified. Standard techniques (e.g., PCR, hybridization) may be used to practice this invention. Such techniques are well known to those of skill in the art.

Also provided by this invention are methods for treating or preventing an HCV infection by monitoring for the mutations provided herein. If a resistance mutant is present in the HCV, then the patient may be treated accordingly. Such a method would comprise: a) collecting a sample (e.g., a plasma sample, PBMC, liver cell, or other sample) from the HCV infected patient; and b) evaluating whether the plasma sample contains nucleic acid encoding HCV NS3/4A protease having a mutation at codon 156; wherein the mutation results in a substitution of alanine with serine. Similar methods could be employed by substituting the 156-alanine to serine mutation with the other mutations set forth herein. Additionally, similar methods could involve identifying the A156 to serine mutation (or other mutation identified herein) and other protease mutation. These methods would all involve, obtaining DNA, amplifying the DNA, and determining the sequence of the DNA.

Also provided by this invention are methods for assessing the effectiveness of NS3/4A protease inhibitor treatment of an HCV infected patient. Such methods comprise: a) collecting a sample (e.g., a plasma sample) from the HCV infected patient; and b) evaluating whether the plasma sample contains nucleic acid encoding HCV NS3/4A protease having a mutation at codon 156; wherein the mutation results in a substitution of alanine with serine. Similar methods may be carried out with the other mutations of this invention.

The methods of this invention are intended to identify resistance mutants in patients that have been administered HCV protease inhibitors. These method may be practiced on a patient that is undergoing treatment or has undergone treatment. These and other diagnostic techniques are known in the art (see, e.g., U.S. Pat. No. 5,631,128 and U.S. Pat. No. 6,489,098).

Accordingly, one embodiment provides a method for evaluating whether a HCV infected patient comprises Hepatitis C virus NS3/4A protease DNA having a mutation at codon 156. Such a patient is likely to be resistant to therapy by an agent such as VX-950. Accordingly, the patient may be treated with a therapy that uses a substitute for VX-950. Another embodiment provides a method for evaluating whether a HCV infected patient comprises Hepatitis C virus NS3/4A protease DNA having a mutation at codon 168.

Certain of these mutations result in a decreased sensitivity or susceptibility to VX-950. Similarly, certain of mutations correlate with or result in decreased sensitivity or susceptibility to BILN 2061 (WO 00/59929; U.S. Pat. No. 6,608,027). Other mutations result in decrease sensitivity or susceptibility to both VX-950 and BILN 2061. Decreased sensitivity or susceptibility to either or both compound could be evaluated according to this invention. By knowing the resistance mutation patterns, more effective treatment regimes may be developed.

For example, this invention allows the design and/or discovery of compounds that are active against the resistance mutants set forth herein.

According, this invention provides a method for evaluating a candidate or potential HCV inhibitor comprising:

a) introducing a vector comprising DNA according to this invention and an indicator gene encoding an indicator into a host cell;

b) culturing the host cell; and c) measuring the indicator in the presence of inhibitor and in the absence of inhibitor.

In this method the test compound may be added in any one or more of steps a)-c).

Another embodiment of this invention provides a method for assaying compounds for activity against HCV comprising:

a) providing a protease according to this invention and a protease substrate;

b) contacting the protease with a candidate or potential inhibitor in the presence of the substrate; and d) evaluating or measuring the inhibition of proteolytic activity of the protease.

Another embodiment of this invention provides a method for identifying an inhibitor of a protease according to this invention comprising:

a) assaying the activity of the protease in the absence of the compound;

b) assaying the activity of the protease in the presence of compound; and c) comparing the results of a) and the results of b). Such a method may further comprise:

d) assaying the activity of a wild-type protease in the absence of the compound;

e) assaying the activity of the wild-type protease in the presence of compound; and f) comparing the results of d) and the results of e). The data from these methods could them be analyzed by, for example, comparing the results from a) and/or b) and the results of d) and/or e).

Also provided are methods comprising:

d) assaying the activity of a second NS3/4A protease comprising amino acid 168 of the protease, wherein amino acid 168 is valine, alanine, glycine, or tyrosine in the absence of the compound;

e) assaying the activity of the second protease in the presence of compound; and f) comparing the results of d) and e). The method may further comprise:

g) assaying the activity of a wild-type protease in the absence of the compound;

h) assaying the activity of the wild-type protease in the presence of compound;

i) comparing the results of g) and the results of h). In a more specific embodiment, the method comprises comparing the results from a) and/or b) and the results of d) and/or e); and/or the results from g) and/or h).

After viruses become resistant to a drug, it is possible that the virus could further mutate and once again become susceptible to the drug. One way this occurs is through the virus coming into contact with a second drug. Accordingly, this invention also provides a method for identifying a compound able to rescue the activity of VX-950, wherein a NS3/4A protease has become resistant to VX-950 comprising:

a) contacting a mutant protease described herein with the compound of interest;

b) assaying the ability of VX-950 to inhibit the activity of the protease of a). Also provided are similar methods for rescuing the activity of BILN 2061 against resistant mutants and/or of VX-950 and BILN 2061 doubly-resistant mutants.

Another aspect to drug resistant viruses, is that this virus may be treatable with another drug. Therefore, methods for identifying compounds that are active against the drug resistant virus are very useful drug discovery tools. Methods described herein may be applied in high through-put screening techniques. Alternatively, the invention also provides methods for carrying out rational drug design techniques. Using structural information about the HCV NS3/4A protease elucidated herein (i.e., that mutation of particular residues at 156 and/or 168 of the wild-type protein) as a basis for the design of effective protease inhibitors. More specifically, the present invention for the first time identifies that HCV strains that are resistant to treatment by protease inhibitors such as VX-950 and BILN 2061.

Rational drug design also may be combined with a systematic method of large-scale screening experiments where potential protease inhibitor drug targets are tested with compounds from combinatorial libraries.

Rational drug design is a focused approach, which uses information about the structure of a drug receptor or one of its natural ligands to identify or create candidate drugs. The three-dimensional structure of a protein can be determined using methods such as X-ray crystallography or nuclear magnetic resonance spectroscopy. In the present invention, the three dimensional structure of a HCV NS3/4A protease mutant that contains one, other or both of the mutations of residues 156 or 168 may now readily be determined using routine X-ray crystallographic and/or NMR spectroscopy techniques.

Rational drug design also may be combined with a systematic method of large-scale screening experiments where potential protease inhibitor drug targets are tested with compounds from combinatorial libraries. Armed with the information provided herein, the skilled artisan may employ computer programs to search through databases containing the structures of many different chemical compounds. The computer can select those compounds that are most likely to interact with the HCV NS3/4A protease from the drug-resistant mutants and test such identified compound in routine laboratory tests from protease inhibitors such as the tests described herein.

In certain embodiments, it is contemplated that the structure of VX-950 or BILN 2061 (see FIG. 4) may be used as a starting structure from which additional molecules may be designed. It is shown herein that the mutant proteases are such that the interaction of VX-950 is reduced. Structures derived from VX-950 that more readily fit into, and interact with the three dimensional structure created when residue 156 is a valine, serine or threonine and/or residue 168 is a valine, alanine, glycine or glutamic acid will be useful new protease inhibitors that can be employed against the resistant strains of HCV in which there is a mutation in the HCV NS3/4A protease. Such compounds also may be effective against wild-type HCV strains in which the HCV NS3/4A protease is not mutated. The teachings of the present invention allow the skilled artisan to focus and narrow the search as much as possible to limit the expense of large-scale screening.

In particular embodiments, the structure of the starting compound has a structure of VX-950 (shown below in structure B). Although VX-950 is exemplified, any stereoisomer of 950 could be used, with mixtures of the D- and L-isomers at the n-propyl side chain being expressly included. The following structure, Structure A depicts such diastereoisomer. This is a mixture of compounds of Structure B (VX-950) and Structure C.

Structure A

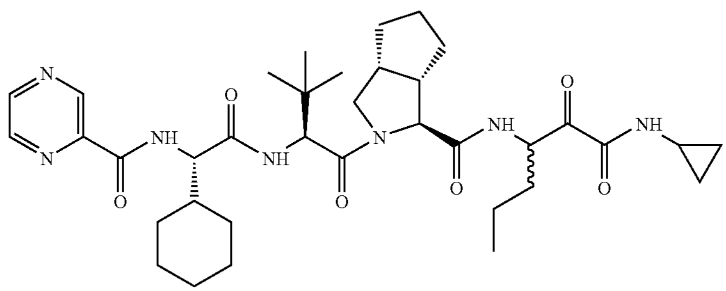

Structure B

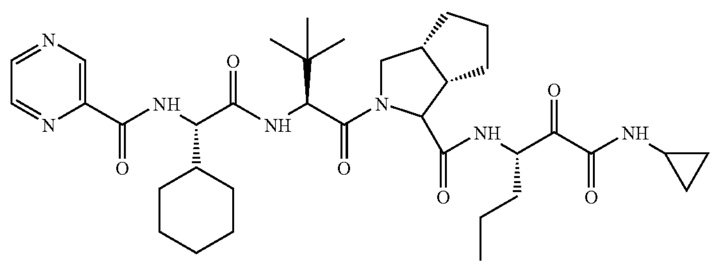

Structure C

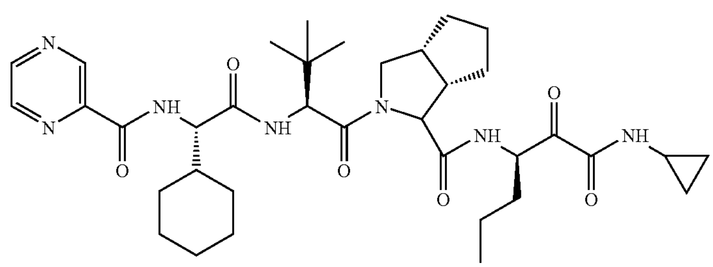

Rational drug design may be used to serially modify different positions on this molecule to produce derivatives thereof that may be useful as protease inhibitors. The crystal structures of the wild-type HCV NS3/4A protease with the VX-950 bound thereto is shown in FIG. 1. The data shown in that figure shows that removal of negative charge at D168 of HCV NS3/4A protease results in lack of restriction of R155 and consequent loss of stacking with the large P2 of BILN 2061 and increase in the cost of desolvation. R155 is not restricted by D168 in the VX-950 —resolved structure and the D168V mutation does not affect its binding. Such binding studies may readily be performed with derivatives elucidated through rational drug design to identify agents that have a binding capacity and/or therapeutic efficacy in the mutants.

Rational drug design has previously been used to identify Relenza, which is used to treat influenza. Design leading to the discovery Relenza was developed by choosing molecules that were most likely to interact with neuraminidase, a virus-produced enzyme that is required to release newly formed viruses from infected cells. Many recent drugs for the treatment of HIV infections (e.g. Ritonivir™, Indinavir™) also were identified through rational drug design schemes in which the drugs were designed to interact with the viral protease, the enzyme that splits up the viral proteins and allows them to assemble properly.

Another well-known drug that was produced by ligand-based rational design is Viagra™. This drug was designed to resemble cGMP, a ligand that binds to phosphodiesterase.

Given that techniques of rational drug design have proven effective once the structure of the target of the drug is known, it is contemplated that the discoveries of the present invention, which reveal the structures of the HCV NS3/4A protease that appear in HCV strains that are resistant to know HCV protease inhibitors, it is contemplated that those of skill in the art will be able to use rational drug design to identify drugs useful for the treatment of HCV.

Accordingly, provided by this invention is also a method for identifying a compound effective against a protease of this invention comprising:

a) obtaining a three dimensional model of the protease;

b) designing or selecting a compound;

c) evaluating the ability of the compound to bind to or interact with the protease.

In such methods, the three dimensional model is based on the x-ray crystal structure (FIG. 1 and FIG. 2) of NS3/4A protease. Methods are known for developing models from crystal structure by, for example, computer-implemented methods molecular modeling (see, e.g., U.S. Pat. No. 6,162,613, WO 98/11134, and/or WO 02/068933). A three dimensional model may also be obtained by x-ray crystallography of a protein according to this invention. As is recognized in the art, a protein may be crystallized in the presence of the absence of a ligand (such as a compound being evaluated).

Evaluating the ability of the compound to bind to, or interact with, the protease is known in the art (see, e.g., U.S. Pat. No. 6,162,613, WO 98/11134, and/or WO 02/068933). The evaluating may be done by, e.g., molecular modeling. After the compound is selected, it may be tested in standard assays, or assays provided herein, to determine the compounds effects of various HCV proteases.

Thus, given the teachings of the present invention, it will be possible to perform screening assays to identify protease inhibitors that are effective against drug resistant HCV infections. The present invention shows that drug-resistance is induced in those HCV strains that have a mutation in either residue 156 or 168 of the HCV NS3/4A protease. More particularly, it has been shown herein that a mutation of A156 to serine, valine, or threonine, and/or a mutation of D168 to a valine, alanine, glycine or glutamic acid results in the HCV being resistant to drug treatment.

It is contemplated that compositions that act as inhibitors of mutant HCV NS3/4A proteases that comprise one or more of the above-articulated mutation will be useful in therapeutic embodiments for the treatment of HCV. The compounds may be those that have been designed to mimic the action of VX-950 or BILN 2061, or are derived from VX-950 or BILN 2061. In the screening assays to identify such compounds, the candidate substance may first be screened for basic biochemical activity in vitro, and then tested for its ability to reduce, ameliorate or otherwise therapeutically intervene in HCV infection in an in vivo model of HCV infection. The mutant proteases of the invention possess protease activity. Any of the screening assays may be set up to determine mutant HCV NS3/4A protease activity using any conventional assay used to determine wild-type HCV NS3/4A protease activity. In preferred embodiments, the activity of the inhibitors against the mutant HCV NS3/4A protease is compared with the activity of the inhibitors against wild-type HCV NS3/4A protease.

The ability of the candidate substance to inhibit the protease is determined by obtaining a sample comprising a HCV NS3/4A protease; and contacting the sample with the candidate substance. The HCV protease activity in the presence and absence of the candidate substance is determined. The protease may be an isolated protein, a membrane fraction comprising the isolated protein, or it may be within a cell that expresses the protease. Thus, the protease activity is typically determined in a protease-containing sample in the absence of the candidate substance. One would then add the candidate substance to the same or a similar composition of the protease-containing sample and determine the protease activity. Any candidate substance which decreases the protease activity of the sample is indicative of the candidate substance having the desired inhibitory activity.

In the in vivo screening assays, the compound is administered to a model animal, over period of time and in various dosages, and an alleviation of the symptoms associated with HCV infection are monitored. Any improvement in one or more of these symptoms will be indicative of the candidate substance being a useful agent.

As used herein the term "candidate substance" refers to any molecule that may potentially act as an inhibitor of the HCV proteases, regardless of whether the proteases are of the wild-type or the mutant variety. Such an agent may be a protein or fragment thereof, a small molecule inhibitor, or even a nucleic acid molecule. It may prove to be the case that the most useful pharmacological compounds will be compounds that are structurally related to other known inhibitors of HCV proteases, such as e.g., VX-950 or BILN 2061 or other inhibitors discussed herein. Rational drug design includes not only comparisons with known such inhibitors, but predictions relating to the structure of target molecules of such inhibitors.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds molded of active, but otherwise undesirable compounds.

Candidate compounds may include fragments or parts of naturally-occurring compounds or may be found as active combinations of known compounds which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or manmade compounds.

"Effective amounts" of the candidate agent in certain circumstances are those amounts effective to reproducibly produce an alteration in the inhibition of HCV NS3/4A protease expression or activity, inhibition of HCV production or virulence, inhibition of HCV infection, or an amelioration or alleviation of one or more of the symptoms of HCV infection in comparison to the levels of these parameters in the absence of such an agent. Compounds that achieve significant appropriate changes in such a parameter will be used. Significant changes in activity and/or expression will be those that are represented by alterations in activity of at least about 30%-40%, and most preferably, by changes of at least about 50%, with higher values of course being possible.

The dominant VX-950 resistant mutant, A156S, remains susceptible to BILN 2061. To confirm whether the observed mutations at either Ala156 or Asp168 are sufficient to confer resistance against VX-950 or BILN 2061, respectively, site-directed mutagenesis was used to introduce each individual mutation at position 156 or 168 into the wild type NS3 protease domain.

Site-specific mutagenesis is another technique useful in the preparation of the mutant protease proteins used in the methods of the invention. This technique employs specific mutagenesis of the underlying DNA (that encodes the amino acid sequence that is targeted for modification). The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids also are routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization (annealing) conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

Of course, the above described approach for site-directed mutagenesis is not the only method of generating potentially useful mutant protease species and as such is not meant to be limiting. The present invention also contemplates other methods of achieving mutagenesis such as for example, treating the recombinant vectors carrying the gene of interest mutagenic agents, such as hydroxylamine, to obtain sequence variants.

The kinetic parameters for the FRET substrate for the wild type NS3 protease domains from genotype 1a and 1b were identical [Table 1A and 1B] under our assay conditions. Although the NS4A peptide co-factor was from HCV genotype 1a, no discernable difference in the kinetic parameters was observed. This is consistent with molecular modeling, which suggests that the conservative variations in the central region of NS4A between genotypes 1a and 1b do not affect the interaction between the NS4A core peptide and the NS3 protease domain. Ki values of VX-950 and BILN 2061 were determined using genotypes 1a and 1b wild type protease, and there were no statistically significant differences between the two wild type proteases (Table 2).

The kinetic parameters of the FRET substrate for the A156S mutant protease were virtually the same as that of the wild type protease (Table 1A and 1B). However, the Ki value of VX-950 was 2.9 μM against the A156S mutant protease, which is 29-fold higher than that against the wild type protease (0.1 μM) (Table 2). BILN 2061 had a Ki value of 112 nM against the A156S mutant, which was 6-fold higher than that against the wild type protease, 19 nM (Table 2).

The HCV RNA level in the replicon cells containing the A156S substitution was similar to that of wild type replicon cells (data not shown), which is consistent with the similar enzymatic catalytic efficiency of the A156S mutant and the wild type NS3 serine proteases. The IC50 value of VX-950 against the A156S replicon cells was 4.65 μM, which is 12 times higher than that against the wild type replicon cells (0.40 μM) (Table 3). The difference between the IC50 values of BILN 2061 against the A156S (7 nM) and the wild type replicon (4 nM) cells was not significant (Table 3).

The major BILN 2061 resistant mutants, D168V and D168A, remain fully susceptible to VX-950.

The substrate kinetic parameters were not affected by the D168V mutation, and showed only minor changes (less than 10-fold) for the D168A mutant as indicated by the comparison of the kcat and kcat/Km values of the wild type and the two mutant NS3 serine proteases (Table 1A and 1B). Similarly, no significant effect of either substitution at Asp168 was observed on the Ki value of VX-950 (Table 2). However, the substitution of valine or alanine for aspartic acid at position 168 resulted in a mutant NS3 protease that was not inhibited by up to 1.2 μM BILN 2061 (Table 2). These data indicate that either mutant protease is at least 63-fold less susceptible to BILN 2061 as compared to the wild type protease. The actual magnitude of resistance cannot be determined since BILN 2061 was not soluble at concentrations greater than 1.2 μM in the assay buffer, as measured by the absorbance at 650 nm. The D168V or D168A mutation was also introduced into the wild type HCV replicon by site-directed mutagenesis and a stable replicon cell line carrying either substitution was generated. BILN 2061 had an IC50 of 5.09 μM against the D168V replicon cells, which is more than 1,300 times higher than against wild type replicon cells (4 nM) (Table 3). The IC50 of BILN 2061 was 1.86 µM against the D168A mutant replicon. There was little change in IC50 values of VX-950 against the D168V and the wild type replicon cells (Table 3).

Accordingly, also provided are compounds identified by the methods of this invention, wherein the compound is an inhibitor of a HCV NS3/4A protease. Such compounds may be generated through for example, rational drug design as discussed above.

The invention also provides compositions that comprise the above compounds and the use thereof. Such compositions may be used to pre-treat invasive devices to be inserted into a patient, to treat biological samples, such as blood, prior to administration to a patient, and for direct administration to a patient. In each case the composition will be used to inhibit HCV replication and to lessen the risk of or the severity of HCV infection.

Another embodiment of this invention provides a composition comprising a compound identified in accordance with this invention or a pharmaceutically acceptable salt thereof. According to a preferred embodiment, the compound identified in accordance with this invention is present in an amount effective to decrease the viral load in a sample or in a patient, wherein said virus encodes a serine protease necessary for the viral life cycle, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2 hydroxyethanesulfonate, lactate, maleate, methanesulfonate, 2 naphthalenesulfonate, nicotinate, oxalate, pamoate, pectinate, persulfate, 3 phenyl propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl D-glucamine, and salts with amino acids such as arginine, lysine, and so forth.

Also, the basic nitrogen containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose based substances, polyethylene glycol, sodium carboxymethylcellulose, polyacrylates, waxes, polyethylene polyoxypropylene block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra articular, intra synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non toxic parenterally acceptable diluent or solvent, for example as a solution in 1,3 butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono or di glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Dosage levels of between about 0.01 and about 100 mg/kg body weight per day, preferably between about 0.5 and about 75 mg/kg body weight per day of the protease inhibitor compounds described herein are useful in a monotherapy for the prevention and treatment of antiviral, particularly anti-HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of identified in accordance with this invention and one or more additional therapeutic or prophylactic agents, both the compound and the additional agent should be present at dosage levels of between about 10 to 100%, and more preferably between about 10 to 80% of the dosage normally administered in a monotherapy regimen.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferred are pharmaceutical compositions formulated for oral administration.

In another embodiment, the compositions of this invention additionally comprise another anti-viral agent, preferably an anti-HCV agent. Such anti-viral agents include, but are not limited to, immunomodulatory agents, such as α-, β-, and γ-interferons, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., compounds of U.S. Pat. Nos. 5,807,876, 6,498,178, 6,344,465, 6,054,472, WO 97/40028, WO 98/40381, WO 00/56331, and mycophenolic acid and derivatives thereof, and including, but not limited to VX-497, VX-148, and/or VX-944); or combinations of any of the above. See also W. Markland et al., Antimicrobial & Antiviral Chemotherapy, 44, p. 859 (2000) and U.S. Pat. No. 6,541,496.

The following definitions are used herein (with trademarks referring to products available as of this application's filing date).

"Peg-Intron" means PEG-Intron®, peginteferon alfa-2b, available from Schering Corporation, Kenilworth, N.J.; "Intron" means Intron-A®, interferon alfa-2b available from Schering Corporation, Kenilworth, N.J.; "ribavirin" means ribavirin (1-beta-D-ribofuranosyl-1H-1,2,4-triazole-3-carboxamide, available from ICN Pharmaceuticals, Inc., Costa Mesa, Calif.; described in the Merck Index, entry 8365, Twelfth Edition; also available as Rebetol® from Schering Corporation, Kenilworth, N.J., or as Copegus® from Hoffmann-La Roche, Nutley, N.J.; "Pagasys" means Pegasys®, peginterferon alfa-2a available Hoffmann-La Roche, Nutley, N.J.; "Roferon" mean Roferon®, recombinant interferon alfa-2a available from Hoffmann-La Roche, Nutley, N.J.; "Berefor" means Berefor®, interferon alfa 2 available from Boehringer Ingelheim Pharmaceutical, Inc., Ridgefield, Conn.; Sumiferon®, a purified blend of natural alpha interferons such as Sumiferon available from Sumitomo, Japan; Wellferon®, interferon alpha n1 available from Glaxo_Wellcome LTd., Great Britain; Alferon®, a mixture of natural alpha interferons made by Interferon Sciences, and available from Purdue Frederick Co., CT.

The term "interferon" as used herein means a member of a family of highly homologous species-specific proteins that inhibit viral replication and cellular proliferation, and modulate immune response, such as interferon alpha, interferon beta, or interferon gamma. The Merck Index, entry 5015, Twelfth Edition. According to one embodiment of the present invention, the interferon is α-interferon. According to another embodiment, a therapeutic combination of the present invention utilizes natural alpha interferon 2a. Alternatively, the therapeutic combination of the present invention utilizes natural alpha interferon 2b. In another embodiment, the therapeutic combination of the present invention utilizes recombinant alpha interferon 2a or 2b.

In yet another embodiment, the interferon is pegylated alpha interferon 2a or 2b. Interferons suitable for the present invention include:

(a) Intron (interferon-alpha 2B, Schering Plough), (b) Peg-Intron, (c) Pegasys, (d) Roferon, (e) Berefor, (f) Sumiferon,
(g) Wellferon,
(h) consensus alpha interferon available from Amgen, Inc., Newbury Park, Calif.,
(i) Alferon;
(j) Viraferon®;
(k) Infergen®.

As is recognized by skilled practitioners, a protease inhibitor would be preferably administered orally. Interferon is not typically administered orally. Nevertheless, nothing herein limits the methods or combinations of this invention to any specific dosage forms or regime. Thus, each component of a combination according to this invention may be administered separately, together, or in any combination thereof.

In one embodiment, the protease inhibitor and interferon are administered in separate dosage forms. In one embodiment, any additional agent is administered as part of a single dosage form with the protease inhibitor or as a separate dosage form. As this invention involves a combination of compounds, the specific amounts of each compound may be dependent on the specific amounts of each other compound in the combination. As recognized by skilled practitioners, dosages of interferon are typically measured in IU (e.g., about 4 million IU to about 12 million IU).

Accordingly, agents (whether acting as an immunomodulatory agent or otherwise) that may be used in combination with a compound of this invention include, but are not limited to, interferon-alpha 2B (Intron A, Schering Plough); Rebatron (Schering Plough, Inteferon-alpha 2B+Ribavirin); pegylated interferon alpha (Reddy, K. R. et al. "Efficacy and Safety of Pegylated (40-kd) interferon alpha-2a compared with interferon alpha-2a in noncirrhotic patients with chronic hepatitis C (Hepatology, 33, pp. 433-438 (2001); consensus interferon (Kao, J. H., et al., "Efficacy of Consensus Interferon in the Treatment of Chronic Hepatitis" J. Gastroenterol. Hepatol. 15, pp. 1418-1423 (2000), interferon-alpha 2A (Roferon A; Roche), lymphoblastoid or "natural" interferon; interferon tau (Clayette, P. et al., "IFN-tau, A New Interferon Type I with Antiretroviral activity" Pathol. Biol. (Paris) 47, pp. 553-559 (1999); interleukin 2 (Davis, G. L. et al., "Future Options for the Management of Hepatitis C." Seminars in Liver Disease, 19, pp. 103-112 (1999); Interleukin 6 (Davis et al. "Future Options for the Management of Hepatitis C." Seminars in Liver Disease 19, pp. 103-112 (1999); interleukin 12 (Davis, G. L. et al., "Future Options for the Management of Hepatitis C." Seminars in Liver Disease, 19, pp. 103-112 (1999); Ribavirin; and compounds that enhance the development of type 1 helper T cell response (Davis et al., "Future Options for the Management of Hepatitis C." Seminars in Liver Disease, 19, pp. 103-112 (1999). Interferons may ameliorate viral infections by exerting direct antiviral effects and/or by modifying the immune response to infection. The antiviral effects of interferons are often mediated through inhibition of viral penetration or uncoating, synthesis of viral RNA, translation of viral proteins, and/or viral assembly and release.

Compounds that stimulate the synthesis of interferon in cells (Tazulakhova, E. B. et al., "Russian Experience in Screening, analysis, and Clinical Application of Novel Interferon Inducers" J. Interferon Cytokine Res., 21 pp. 65-73) include, but are not limited to, double stranded RNA, alone or in combination with tobramycin, and Imiquimod (3M Pharmaceuticals; Sauder, D. N. "Immunomodulatory and Pharmacologic Properties of Imiquimod" J. Am. Acad. Dermatol., 43 pp. S6-11 (2000).

Other non-immunomodulatory or immunomodulatory compounds may be used in combination with a compound of this invention including, but not limited to, those specified in WO 02/18369, which is incorporated herein by reference (see, e.g., page 273, lines 9-22 and page 274, line 4 to page 276, line 11, which is incorporated herein by reference in its entirety).

Compounds that stimulate the synthesis of interferon in cells (Tazulakhova et al., J. Interferon Cytokine Res. 21, 65-73)) include, but are not limited to, double stranded RNA, alone or in combination with tobramycin and Imiquimod (3M Pharmaceuticals) (Sauder, J. Am. Arad. Dermatol. 43, S6-11 (2000)).

Other compounds known to have, or that may have, HCV antiviral activity by virtue of non-immunomodulatory mechanisms include, but are not limited to, Ribavirin (ICN Pharmaceuticals); inosine 5'-monophosphate dehydrogenase inhibitors (VX-497 formula provided herein); amantadine and rimantadine (Younossi et al., In Seminars in Liver Disease 19, 95-102 (1999)); LY217896 (U.S. Pat. No. 4,835,168) (Colacino, et al., Antimicrobial Agents & Chemotherapy 34, 2156-2163 (1990)); and 9-Hydroxyimino-6-methoxy-1,4a-dimethyl1,2,3,4,4a,9,10,10a-octahydro-phenanthrene-1-carboxylic acid methyl ester; 6-Methoxy-1,4a dimethyl-9-(4-methyl-piperazin-1-ylimino)-1,2,3,4,4a,9,10,10a-octahydro-phenanthrene-1carboxylic acid methyl ester-hydrochloride; 1-(2-Chloro-phenyl)-3-(2,2-Biphenyl-ethyl)-urea (U.S. Pat. No. 6,127,422).

Formulations, doses, and routes of administration for the foregoing molecules are either taught in the references cited below, or are well-known in the art as disclosed, for example, in F. G. Hayden, in Goodman & Gilman's The Pharmacological Basis of Therapeutics, Ninth Edition, Hardman et al., Eds., McGraw-Hill, New York (1996), Chapter 50, pp. 1191-1223, and the references cited therein. Alternatively, once a compound that exhibits HCV antiviral activity, particularly antiviral activity against a drug-resistant strain of HCV, has been identified, a pharmaceutically effective amount of that compound can be determined using techniques that are well-known to the skilled artisan. Note, for example, Benet et al., in Goodman & Gilman's The Pharmacological Basis of Therapeutics, Ninth Edition, Hardman et al., Eds., McGraw-Hill, New York (1996), Chapter 1, pp. 3-27, and the references cited therein. Thus, the appropriate formulations, dose(s) range, and dosing regimens, of such a compound can be easily determined by routine methods.

The drug combinations of the present invention can be provided to a cell or cells, or to a human patient, either in separate pharmaceutically acceptable formulations administered simultaneously or sequentially, formulations containing more than one therapeutic agent, or by an assortment of single agent and multiple agent formulations. Regardless of the route of administration, these drug combinations form an anti-HCV effective amount of components of the pharmaceutically acceptable formulations.

A large number of other immunomodulators and immunostimulants that can be used in the methods of the present invention are currently available and include: AA-2G; adamantylamide dipeptide; adenosine deaminase, Enzon adjuvant, Alliance; adjuvants, Ribi; adjuvants, Vaxcel; Adjuvax; agelasphin-11; AIDS therapy, Chiron; algal glucan, SRI; alganunulin, Anutech; Anginlyc; anticellular factors, Yeda; Anticort; antigastrin-17 immunogen, Ap; antigen delivery system, Vac; antigen formulation, IDBC; antiGnRH immunogen, Aphton; Antiherpin; Arbidol; azarole; Bay-q-8939; Bay-r-1005; BCH-1393; Betafectin; Biostim; BL-001; BL-009; Broncostat; Cantastim; CDRI-84-246; cefodizime; chemokine inhibitors, ICOS; CMV peptides, City of Hope; CN-5888; cytokine-releasing agent, St; DHEAS, Paradigm;

DISC TA-HSV; J07B; I01A; I01Z; ditiocarb sodium; ECA-10-142; ELS-1; endotoxin, Novartis; FCE-20696; FCE-24089; FCE-24578; FLT-3 ligand, Immunex; FR-900483; FR-900494; FR-901235; FTS-Zn; G-proteins, Cadus; gludapcin; glutaurine; glycophosphopeptical; GM-2; GM-53; GMDP; growth factor vaccine, EntreM; H-BIG, NABI; H-CIG, NABI; HAB-439; *Helicobacter pylori* vaccine; herpes-specific immune factor; HIV therapy, United Biomed; HyperGAM+CF; ImmuMax; Immun BCG; immune therapy, Connective; immunomodulator, Evans; immunomodulators, Novacell; imreg-1; imreg-2; Indomune; inosine pranobex; interferon, Dong-A (alpha2); interferon, Genentech (gamma); interferon, Novartis (alpha); interleukin-12, Genetics Ins; interleukin-15, Immunex; interleukin-16, Research Cor; ISCAR-1; J005X; L-644257; licomarasminic acid; LipoTher; LK-409, LK-410; LP-2307; LT (R1926); LW-50020; MAF, Shionogi; MDP derivatives, Merck; met-enkephalin, TNI; methylfurylbutyrolactones; MIMP; mirimostim; mixed bacterial vaccine, Tem, MM-1; moniliastat; MPLA, Ribi; MS-705; murabutide; marabutide, Vacsyn; muramyl dipeptide derivative; muramyl peptide derivatives myelopid; –563; NACOS-6; NH-765; NISV, Proteus; NPT-16416; NT-002; PA-485; PEFA-814; peptides, Scios; peptidoglycan, Pliva; Perthon, Advanced Plant; PGM derivative, Pliva; Pharmaprojects No. 1099; No. 1426; No. 1549; No. 1585; No. 1607; No. 1710; No. 1779; No. 2002; No. 2060; No. 2795; No. 3088; No. 3111; No. 3345; No. 3467; No. 3668; No. 3998; No. 3999; No. 4089; No. 4188; No. 4451; No. 4500; No. 4689; No. 4833; No. 494; No. 5217; No. 530; pidotimod; pimelautide; pinafide; PMD-589; podophyllotoxin, Conpharm; POL-509; poly-ICLC; poly-ICLC, Yamasa Shoyu; PolyA-PolyU; Polysaccharide A; protein A, Berlux Bioscience; PS34W0; Pseudomonas MAbs, Teijin; Psomaglobin; PTL-78419; Pyrexol; pyriferone; Retrogen; Retropep; RG-003; Rhinostat; rifamaxil; RM-06; Rollin; romurtide; RU-40555; RU-41821; Rubella antibodies, ResCo; S-27649; SB-73; SDZ-280-636; SDZ-MRL953; SK&F-107647; SL04; SL05; SM-4333; Solutein; SRI-62-834; SRL-172; ST-570; ST-789; staphage lysate; Stimulon; suppressin; T-150R1; T-LCEF; tabilautide; temurtide; Theradigm-HBV; Theradigm-HBV; Theradigm-HSV; THF, Pharm & Upjohn; THF, Yeda; thymalfasin; thymic hormone fractions; thymocartin; thymolymphotropin; thymopentin; thymopentin analogues; thymopentin, Peptech; thymosin fraction 5, Alpha; thymostimulin; thymotrinan; TMD-232; TO-115; transfer factor, Viragen; tuftsin, Selavo; ubenimex; Ulsastat; ANGG−; CD-4+; Collag+; COLSF+; COM+; DA-A+; GAST−; GF-TH+; GP-120−; IF+; IF-A+; IF-A-2+; IF-B+; IF-G+; IF-G-1B+; IL-2+; IL-12+; IL-15+; IM+; LHRH−; LIPCOR+L LYM-B+; LYM-NK+; LYM-T+; OPI+; PEP+; PHG-MA+; RNA-SYN−; SY-CW−; TH-A-I+; TH-5+; TNF+; UN.

Representative nucleoside and nucleotide compounds useful in the present invention include, but are not limited to: (+)-cis-5-fluoro-1-[2-(hydroxy-methyl)-[1,3-oxathiolan-5yl]cytosine; (−)-2'-deoxy-3'-thiocytidine-5'-triphospbate (3TC); (−)-cis-5-fluoro-1-[2(hydroxy-methyl)-[1,3-oxathiolan-5-yl]cytosine (FTC); (−)2', 3', dideoxy-3'-thiacytidine [(−)-SddC]; 1-(2'-deoxy-2'-fluoro-beta-D-arabinofuranosyl)-5-iodocytosine (FIAC); 1-(2'-deoxy-2'-fluoro-beta-D-arabinofuranosyl)-5-iodocytosine triphosphate (FIACTP); 1-(2'-deoxy-2'-fluoro-beta-D-arabinofuranosyl)-5-methyluracil (FMAU); 1-beta-D-ribofuranosyl-1,2,4-triazole-3-carboxamide; 2',3'-dideoxy-3'-fluoro-5-methyl-dexocytidine (FddMeCyt); 2',3'-dideoxy-3'-chloro-5-methyl-dexocytidine (ClddMeCyt); 2',3'-dideoxy-3'-amino-5-methyl-dexocytidine (AddMeCyt); 2',3'-dideoxy-3'-fluoro-5-methyl-cytidine (FddMeCyt); 2',3'-dideoxy-3'-chloro-5-methyl-cytidine (ClddMeCyt); 2',3'-dideoxy-3'-amino-5-methyl-cytidine (AddMeCyt); 2',3'-dideoxy-3'-fluorothymidine (FddThd); 2',3'-dideoxy-beta-L-5-fluorocytidine (beta-L-FddC) 2',3'-dideoxy-beta-L-5-thiacytidine; 2',3'-dideoxy-beta-L-5-cytidine (beta-L-ddC); 9-(1,3-dihydroxy-2-propoxymethyl) guanine; 2'-deoxy-3'-thia-5-fluorocytosine; 3'-amino-5-methyl-dexocytidine (AddMeCyt); 2-amino-1,9-[(2-hydroxymethyl-1-(hydroxymethyl) ethoxy]methyl]-6H-purin-6-one (gancyclovir); 2-[2-(2-amino-9H-purin-9y) ethyl)-1,3-propandil diacetate(famciclovir); 2-amino-1,9-dihydro-9-[(2-hydroxy-ethoxy) methyl]6H-purin-6-one (acyclovir); 9-(4-hydroxy-3-hydroxymethyl-but-1-yl) guanine (penciclovir); 9-(4-hydroxy-3-hydroxymethyl-but-1-yl)-6-deoxy-guanine diacetate(famciclovir); 3'-azido-3'-deoxythymidine (AZT); 3'-chloro-5-methyl-dexocytidine (ClddMeCyt); 9-(2-phosphonyl-methoxyethyl)-2',6'-diaminopurine-2', 3'-dideoxyriboside; 9-(2-phosphonylmethoxyethyl)adenine (PMEA); acyclovir triphosphate (ACVTP); D-carbocyclic-2'-deoxyguanosine (CdG); dideoxy-cytidine; dideoxy-cytosine (ddC); dideoxy-guanine (ddG); dideoxy-inosine (ddI); E-5-(2-bromovinyl)-2'-deoxyuridine triphosphate; fluoro-arabinofuranosyl-iodouracil; 1-(2'-deoxy-2'-fluoro-1-beta-D-arabinofuranosyl)-5-iodo-uracil (FIAU); stavudine; 9-beta-D-arabinofuranosyl-9H-purine-6-amine monohydrate (Ara-A); 9-beta-D-arabinofuranosyl-9H-purine-6-amine-5'-monophosphate monohydrate (Ara-AMP); 2-deoxy-3'-thia-5-fluorocytidine; 2',3'-dideoxy-guanine; and 2',3'-dideoxy-guanosine.

Synthetic methods for the preparation of nucleosides and nucleotides useful in the present invention are well known in the art as disclosed in Acta Biochim Pol., 43, 25-36 (1996); Swed. Nucleosides Nucleotides 15, 361-378 (1996); Synthesis 12, 1465-1479 (1995); Carbohyd. Chem. 27, 242-276 (1995); Chena Nucleosides Nucleotides 3, 421-535 (1994); Ann. Reports in Med. Chena, Academic Press; and Exp. Opin. Invest. Drugs 4, 95-115 (1995).

The chemical reactions described in the references cited above are generally disclosed in terms of their broadest application to the preparation of the compounds of this invention. Occasionally, the reactions may not be applicable as described to each compound included within the scope of compounds disclosed herein. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional will be applicable to the preparation of the corresponding compounds of this invention. In all preparative methods, all starting materials are known or readily preparable from known starting materials.

While nucleoside analogs are generally employed as antiviral agents as is, nucleotides (nucleoside phosphates) sometimes have to be converted to nucleosides in order to facilitate their transport across cell membranes. An example of a chemically modified nucleotide capable of entering cells is S-1-3-hydroxy-2-phosphonylmethoxypropyl cytosine (HP-MPC, Gilead Sciences). Nucleoside and nucleotide compounds used in this invention that are acids can form salts. Examples include salts with alkali metals or alkaline earth metals, such as sodium, potassium, calcium, or magnesium, or with organic bases or basic quaternary ammonium salts.

The skilled artisan may also chose to administer a cytochrome P450 monooxygenase inhibitor. Such inhibitors may be useful in increasing liver concentrations and/or increasing blood levels of compounds that are inhibited by cytochrome P450.

If an embodiment of this invention involves a CYP inhibitor, any CYP inhibitor that improves the pharmacokinetics of the relevant NS3/4A protease may be used in a method of this invention. These CYP inhibitors include, but are not limited to, ritonavir (WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methylpyrazole, cyclosporin, and clomethiazole. For preferred dosage forms of ritonavir, see U.S. Pat. No. 6,037,157, and the documents cited therein: U.S. Pat. No. 5,484,801, U.S. application Ser. No. 08/402,690, and International Applications WO 95/07696 and WO 95/09614).

Methods for measuring the ability of a compound to inhibit cytochrome P50 monooxygenase activity are known (see U.S. Pat. No. 6,037,157 and Yun, et al. Drug Metabolism & Disposition, vol. 21, pp. 403-407 (1993).

Immunomodulators, immunostimulants and other agents useful in the combination therapy methods of the present invention can be administered in amounts lower than those conventional in the art. For example, interferon alpha is typically administered to humans for the treatment of HCV infections in an amount of from about $1\times10^6$ units/person three times per week to about $10\times10^6$ units/person three times per week (Simon et al., Hepatology 25: 445-448 (1997)). In the methods and compositions of the present invention, this dose can be in the range of from about $0.1\times10^6$ units/person three times per week to about $7.5\times10^6$ units/person three times per week; more preferably from about $0.5\times10^6$ units/person three times per week to about $5\times10^6$ units/person three times per week; most preferably from about $1\times10^6$ units/person three times per week to about $3\times10^6$ units/person three times per week. Due to the enhanced hepatitis C virus antiviral effectiveness of immunomodulators, immunostimulants or other anti-HCV agent in the presence of the HCV serine protease inhibitors of the present invention, reduced amounts of these immunomodulators/immunostimulants can be employed in the treatment methods and compositions contemplated herein. Similarly, due to the enhanced hepatitis C virus antiviral effectiveness of the present HCV serine protease inhibitors in the presence of immunomodulators and immunostimulants, reduced amounts of these HCV serine protease inhibitors can be employed in the methods and compositions contemplated herein. Such reduced amounts can be determined by routine monitoring of hepatitis C virus titers in infected patients undergoing therapy. This can be carried out by, for example, monitoring HCV RNA in patients' serum by slot-blot, dot-blot, or RT-PCR techniques, or by measurement of HCV surface or other antigens. Patients can be similarly monitored during combination therapy employing the HCV serine protease inhibitors disclosed herein and other compounds having anti-HCV activity, for example nucleoside and/or nucleotide antiviral agents, to determine the lowest effective doses of each when used in combination.

In the methods of combination therapy disclosed herein, nucleoside or nucleotide antiviral compounds, or mixtures thereof, can be administered to humans in an amount in the range of from about 0.1 mg/person/day to about 500 mg/person/day; preferably from about 10 mg/person/day to about 300 mg/person/day; more preferably from about 25 mg/person/day to about 200 mg/person/day; even more preferably from about 50 mg/person/day to about 150 mg/person/day; and most preferably in the range of from about 1 mg/person/day to about 50 mg/person/day.

Doses of compounds can be administered to a patient in a single dose or in proportionate doses. In the latter case, dosage unit compositions can contain such amounts of submultiples thereof to make up the daily dose. Multiple doses per day can also increase the total daily dose should this be desired by the person prescribing the drug.

The regimen for treating a patient suffering from a HCV infection with the compounds and/or compositions of the present invention is selected in accordance with a variety of factors, including the age, weight, sex, diet, and medical condition of the patient, the severity of the infection, the route of administration, pharmacological considerations such as the activity, efficacy, pharmacokinetic, and toxicology profiles of the particular compounds employed, and whether a drug delivery system is utilized. Administration of the drug combinations disclosed herein should generally be continued over a period of several weeks to several months or years until virus titers reach acceptable levels, indicating that infection has been controlled or eradicated. Patients undergoing treatment with the drug combinations disclosed herein can be routinely monitored by measuring hepatitis viral RNA in patients' serum by slot-blot, dot-blot, or RT-PCR techniques, or by measurement of hepatitis C viral antigens, such as surface antigens, in serum to determine the effectiveness of therapy. Continuous analysis of the data obtained by these methods permits modification of the treatment regimen during therapy so that optimal amounts of each component in the combination are administered, and so that the duration of treatment can be determined as well. Thus, the treatment regimen/dosing schedule can be rationally modified over the course of therapy so that the lowest amounts of each of the antiviral compounds used in combination which together exhibit satisfactory anti-hepatitis C virus effectiveness are administered, and so that administration of such antiviral compounds in combination is continued only so long as is necessary to successfully treat the infection.

The present invention encompasses the use of the HCV serine protease inhibitors disclosed herein in various combinations with the foregoing and similar types of compounds having anti-HCV activity to treat or prevent HCV infections in patients, particularly those patients that have HCV infections that have developed resistance to treatment by VX-950 and other standard protease inhibitors. For example, one or more HCV serine protease inhibitors can be used in combination with: one or more interferons or interferon derivatives having anti-HCV activity; one or more non-interferon compounds having anti-HCV activity; or one or more interferons or interferon derivatives having anti-HCV activity and one or more non-interferon compounds having anti-HCV activity. When used in combination to treat or prevent HCV infection in a human patient, any of the presently disclosed HCV serine protease inhibitors and foregoing compounds having anti-HCV activity can be present in a pharmaceutically or anti-HCV effective amount. By virtue of their additive or synergistic effects, when used in the combinations described above, each can also be present in a subclinical pharmaceutically effective or anti-HCV effective amount, i.e., an amount that, if used alone, provides reduced pharmaceutical effectiveness in completely inhibiting or reducing the accumulation of HCV virions and/or reducing or ameliorating conditions or symptoms associated with HCV infection or pathogenesis in patients compared to such HCV serine protease inhibitors and compounds having anti-HCV activity when used in pharmaceutically effective amounts. In addition, the present invention encompasses the use of combinations of HCV serine protease inhibitors and compounds having anti-HCV activity as described above to treat or prevent HCV infections, where one or more of these inhibitors or compounds is present in a pharmaceutically effective amount, and the other(s) is(are) present in a subclinical pharmaceutically-effective or anti-HCV effective amount(s) owing to their additive or synergistic effects. As used herein, the term "additive effect" describes the combined effect of two (or more) pharmaceutically active agents that is equal to the sum of the effect of each agent given alone. A synergistic effect is one in which the combined effect of two (or more) pharmaceutically active agents is greater than the sum of the effect of each agent given alone.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional anti-viral agent in the composition.

According to another embodiment, the invention provides a method for treating a patient infected with a virus characterized by a virally encoded serine protease that is necessary for the life cycle of the virus by administering to said patient a pharmaceutically acceptable composition of this invention. Preferably, the methods of this invention are used to treat a patient suffering from a HCV infection. Such treatment may completely eradicate the viral infection or reduce the severity thereof. More preferably, the patient is a human being.

In an alternate embodiment, the methods of this invention additionally comprise the step of administering to said patient an anti-viral agent preferably an anti-HCV agent. Such antiviral agents include, but are not limited to, immunomodulatory agents, such as α-, β-, and γ-interferons, pegylated derivatized interferon-α compounds, and thymosin; other anti-viral agents, such as ribavirin and amantadine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. No. 5,807,876, mycophenolic acid and derivatives thereof); or combinations of any of the above.

Such additional agent may be administered to said patient as part of a single dosage form comprising both a compound of this invention and an additional anti-viral agent. Alternatively the additional agent may be administered separately from the compound of this invention, as part of a multiple dosage form, wherein said additional agent is administered prior to, together with or following a composition comprising a compound of this invention.

In yet another embodiment the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

According to another embodiment the invention provides methods of treating materials that may potentially come into contact with a virus characterized by a virally encoded serine protease necessary for its life cycle. This method comprises the step of contacting said material with a compound according to the invention. Such materials include, but are not limited to, surgical instruments and garments; laboratory instruments and garments; blood collection apparatuses and materials; and invasive devices, such as shunts, stents, etc.

In another embodiment, the compounds of this invention may be used as laboratory tools to aid in the isolation of a virally encoded serine protease. This method comprises the steps of providing a compound of this invention attached to a solid support; contacting said solid support with a sample containing a viral serine protease under conditions that cause said protease to bind to said solid support; and eluting said serine protease from said solid support. Preferably, the viral serine protease isolated by this method is HCV NS3-NS4A protease. More particularly, it is a mutant HCV NS3-NS4A protease that is resistant to treatment by VX-905 and/or BILN 2061 as described herein. Exemplary such proteases includes those described herein as having mutant (i.e., non-wild-type) residues at positions 156 and/or 168 of a protein of SEQ ID NO:2.

As used herein, unless otherwise required, the term "comprise" and variations thereof indicate the inclusion of the stated element, but not the exclusion of any other element.

Routine techniques that are known to skilled practitioners may be used to practice this invention. Such techniques may be found in published documents. For example, standard recombinant DNA and molecular cloning techniques are well known in the art. See, e.g., F. M. Ausubel, Current Protocols in Molecular Biology, John Wiley & Sons, Inc., Media, Pa.; Sambrook, J., Fritsch, E. F. and Maniatis, T., Molecular Cloning: A Laboratory Manual; Cold Spring Harbor Laboratory Press: Cold Spring Harbor, 1989, and the literature documents cited in U.S. Pat. Nos. 6,617,156, and 6,617,130, all of which are hereby incorporated by reference.

EXAMPLES

In order that this invention be more fully understood, the following preparative and testing examples are set forth. The following examples are included to demonstrate certain preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of Plasmids

A DNA fragment encoding residues $Ala^1$-$Ser^{181}$ of the HCV NS3 protease (GenBank CAB46913) was obtained by PCR from the HCV Con1 replicon plasmid, $I_{377}$neo/NS3-3'/wt (re-named as pBR322-HCV-Neo in this study) [V. Lohmann et al., Science, 285, pp. 110-113 (1999)] and inserted into pBEV11 (S. Chamber, et al., personal communication) for expression of the HCV proteins with a C-terminal hexa-histidine tag in E. coli. Resistance mutations against the HCV NS3•4A PI were introduced into this construct by PCR-based, site-directed mutagenesis. To generate the HCV replicon containing the PI-resistant mutations, a 1.2-kb Hind III/BstX I fragment derived from the HCV Con 1 replicon was sub-cloned into a TA cloning vector, pCR2.1 (Invitrogen). The PI-resistant mutations in the NS3 serine protease domain were introduced into the pCR2.1 vector containing the Hind III/BstX I HCV fragment by PCR, and a 579-bp BsrG I/BstX I fragment containing the mutated residue was sub-cloned back into a second generation Con1 replicon plasmid containing three adaptive mutations, pBR322-HCV-Neo-mADE (see below). All constructs were confirmed by sequencing.

Example 2

Generation of HCV Replicon Cells

The Con1 sub-genomic replicon plasmid pBR322-HCV-Neo [Lohmann et al., Science, 285, pp. 110-113 (1999)] was digested with Sca I (New England Biolabs). Full-length HCV sub-genomic replicon RNA was generated from the linearized DNA template using a T7 Mega-script kit (Ambion) and treated with DNase to remove the template DNA. The run-off RNA transcripts were electroporated into Huh-7 cells and stable HCV replicon cell lines were selected with 0.25 or 1 mg per ml G418 (Geneticin) in Dulbecco's modified minimal essential medium (DMEM) containing 10% fetal bovine serum (FBS). HCV replicon stable cells were maintained in DMEM, 10% FBS and 0.25 mg per ml G418.

During the course of generating of the HCV sub-genomic replicon stable cell lines, several different patterns of adaptive mutations were identified. One pattern has three substitutions in the HCV nonstructural proteins, which were introduced into the original pBR322-HCV-Neo plasmid by site-directed mutagenesis to generate the second-generation sub-genomic replicon plasmid, pBR322-HCV-Neo-mADE. When the T7 run-off RNA transcripts from the Sca I-linearized pBR322-HCV-Neo-mADE plasmid were electroporated into Huh7 cells, stable replicon cell colonies were formed at a much higher efficiency than the original Con1 replicon RNA. The resistance mutations identified in this study were introduced into the pBR322-HCV-Neo-mADE replicon plasmid by site-directed mutagenesis. Stable replicon cell lines were generated using the T7 transcripts derived from either wild type pBR322-HCV-Neo-mADE or the ones with the resistance mutations.

Example 3

HCV Replicon Cell Assay Protocol

Cells containing hepatitis C virus (HCV) replicon were maintained in DMEM containing 10% fetal bovine serum (FBS), 0.25 mg per ml of G418, with appropriate supplements (media A).

On day 1, replicon cell monolayer was treated with a trypsin:EDTA mixture, removed, and then media A was diluted into a final concentration of 100,000 cells per ml wit. 10,000 cells in 100 ul were plated into each well of a 96-well tissue culture plate, and cultured overnight in a tissue culture incubator at 37° C.

On day 2, compounds (in 100% DMSO) were serially diluted into DMEM containing 2% FBS, 0.5% DMSO, with appropriate supplements (media B). The final concentration of DMSO was maintained at 0.5% throughout the dilution series.

Media on the replicon cell monolayer was removed, and then media B containing various concentrations of compounds was added. Media B without any compound was added to other wells as no compound controls.

Cells were incubated with compound or 0.5% DMSO in media B for 48 hours in a tissue culture incubator at 37° C. At the end of the 48-hour incubation, the media was removed, and the replicon cell monolayer was washed once with PBS and stored at −80° C. prior to RNA extraction.

Culture plates with treated replicon cell monolayers were thawed, and a fixed amount of another RNA virus, such as Bovine Viral Diarrhea Virus (BVDV) was added to cells in each well. RNA extraction reagents (such as reagents from RNeasy kits) were added to the cells immediately to avoid degradation of RNA. Total RNA was extracted according the instruction of manufacturer with modification to improve extraction efficiency and consistency. Finally, total cellular RNA, including HCV replicon RNA, was eluted and stored at −80° C. until further processing.

A Taqman real-time RT-PCR quantification assay was set up with two sets of specific primers and probe. One was for HCV and the other was for BVDV. Total RNA extractants from treated HCV replicon cells was added to the PCR reactions for quantification of both HCV and BVDV RNA in the same PCR well. Experimental failure was flagged and rejected based on the level of BVDV RNA in each well. The level of HCV RNA in each well was calculated according to a standard curve run in the same PCR plate. The percentage of inhibition or decrease of HCV RNA level due to compound treatment was calculated using the DMSO or no compound control as 0% of inhibition. The cytotoxicity of the compounds was measured using a mitochondrial enzyme-based cell viability assay, CellTiter 96 AQueous One Solution Cell Proliferation Assay (Promega). The $IC_{50}$ (concentration at which 50% inhibition of HCV RNA level is observed) and $CC_{50}$ (concentration at which 50% reduction of cell viability is observed) values were calculated from the titration curve of any given compound using four-parameter curve fitting (Soft-Max Pro).

Example 4

Selection of HCV PI-resistant Replicon Cells

The HCV Con1 sub-genomic replicon stable cells were serially passed in the presence of 0.25 mg per ml G418 and slowly increasing concentrations of VX-950 (series A), BILN 2061 (series B), or combination of both VX-950 and BILN 2061 (series C, D, and E). The concentrations of VX-950 ranged from 3.5 μM (or 10×$IC_{50}$) in the 48-hour assay (see above), to 28 μM (80×$IC_{50}$). For BILN 2061, the starting concentration was 80 nM (80×$IC_{50}$), and the final concentration was 12.5 μM (12,500×$IC_{50}$). During the course of selection, replicon cells were split twice per week when a 70-90% confluence was reached. Fresh HCV PI was added every 3 to 4 days regardless the cell culture was split or not.

Example 5

Identification of HCV PI-resistance Mutations

During the selection of HCV PI-resistant replicon cells, cell pellets were collected every time the cell culture was split. Total cellular RNA was extracted using the RNeasy mini-prep kit (Qiagen). A 1.7-kb long cDNA fragment encompassing the HCV NS3 serine protease region was amplified with a pair of HCV-specific oligonucleotides (5'-CCTTCTATCGCCTTCTTG-3' (SEQ ID NO:3) and 5'-CTTGATGGTCTCGATGG-3' (SEQ ID NO:4)) using the Titan One-Step RT-PCR kit (Roche Applied Science). The amplified products were purified using the QIA-quick PCR purification kit (Qiagen). To monitor the emergence of the HCV PI-related mutations in the HCV NS3 serine protease domain during the selection, the purified 1.7-kb RT-PCR products of PI-treated replicons from several different culture time points were subjected to sequence determination. To determine the frequency of PI-resistant mutations, the 1.7-kb RT-PCR products of HCV RNA of the VX-950 or BILN 2061-resistant replicon cells were ligated into the TA cloning vector pCR2.1 (Invitrogen). For each time point, multiple individual bacterial colonies were isolated and the HCV NS3 protease coding region of the purified plasmid DNA was sequenced.

Example 6

Expression and Purification of the HCV NS3 Serine Protease Domain

Each of the expression constructs for the HCV NS3 serine protease domain containing the wild type sequence or the resistance mutations (A156D, D168V, or D168A) were transformed into BL21/DE3 pLysS E. coli cells (Stratagene). Freshly transformed cells were grown at 37° C. in a BHI medium (Difco Laboratories) supplemented with 100 μg per ml carbenicillin and 35 μg per ml chloramphenicol to an optical density of 0.75 at 600 nM. Induction with 1 mM IPTG was performed for four hours at 24° C. Cell pastes were harvested by centrifugation and flash frozen at −80° C. prior to protein purification. All purification steps were performed at 4° C. For each of the HCV NS3 proteases, 100 g of cell paste was lysed in 1.5 L of buffer A {50 mM HEPES (pH 8.0), 300 mM NaCl, 0.1% n-octyl-β-D-glucopyranoside, 5 mM β-mecaptoethanol, 10% (v/v) glycerol} and stirred for 30 min. The lysates were homogenized using a Microfluidizer (Microfluidics, Newton, Mass.), followed by ultra-centrifugation at 54,000×g for 45 min. Imidazole was added to the supernatants to a final concentration of 5 mM along with 2 ml of Ni-NTA resin pre-equilibrated with buffer A containing 5 mM imidazole. The mixtures were rocked for three hours and washed with 20 column volumes of buffer A plus 5 mM imidazole. The mixtures were rocked for three hours and washed with 20 column volumes of buffer A plus 5 mM imidazole. The HCV NS3 proteins were eluted in buffer A containing 300 mM imidazole. The eluates were concentrated and loaded onto a Hi-Load 16/60 Superdex 200 column, pre-equilibrated with buffer A. The appropriate fractions of the purified HCV proteins were pooled and stored at −80° C.

Example 7

Enzymatic Assays for the HCV NS3 Serine Protease Domain

A HPLC Enzyme Assay Protocol

HPLC Microbore Method for Separation of 5AB Substrate and Products

Substrate:

NH2-Glu-Asp-Val-Val-(alpha)Abu-Cys-Ser-Met-Ser-Tyr-COOH

A stock solution of 20 mM 5AB (or concentration of your choice) was made in DMSO w/0.2M DTT. This was stored in aliquots at −20 C.

Buffer: 50 mM HEPES, pH 7.8; 20% glycerol; 100 mM NaCl

Total assay volume was 100 μL

| | X1 μL | Conc. In assay |
|---|---|---|
| Buffer | 86.5 | See above |
| 5 mM KK4A | 0.5 | 25 μM |
| 1 M DTT | 0.5 | 5 mM |
| DMSO or inhibitor | 2.5 | 2.5% v/v |
| 50 μM tNS3 | 0.05 | 25 nM |
| 250 μM 5AB (initiate) | 20 | 25 μM |

The buffer, KK4A, DTT, and tNS3 were combined; distributed 78 μL each into wells of 96 well plate. This was incubated at 30 C for ~5-10 min.

2.5 μL of appropriate concentration of test compound was dissolved in DMSO (DMSO only for control) and added to each well. This was incubated at room temperature for 15 min.

The reaction was initiated by addition of 20 μL of 250 μM 5AB substrate (25 μM concentration is equivalent or slightly lower than the Km for 5AB). The reaction was incubated for 20 min at 30° C., and then terminated by addition of 25 μL of 10% TFA. 120 μL aliquots of the final reaction end product was transferred to HPLC vials. The SMSY product was separated from substrate and KK4A by the following method:

Microbore Separation Method:
    Instrumentation: Agilent 1100
    Degasser G1322A
    Binary pump G1312A
    Autosampler G1313A
    Column thermostated chamber G1316A
    Diode array detector G1315A
    Column:

Phenomenex Jupiter; 5 micron C18; 300 angstroms; 150×2 mm; P/O 00F-4053-B0.
Column thermostat: 40° C.
Injection volume: 100 μL
Solvent A=HPLC grade water+0.1% TFA
Solvent B=HPLC grade acetonitrile+0.1% TFA

| Time (min) | % B | Flow (ml/min) | Max press. |
|---|---|---|---|
| 0 | 5 | 0.2 | 400 |
| 12 | 60 | 0.2 | 400 |
| 13 | 100 | 0.2 | 400 |
| 16 | 100 | 0.2 | 400 |
| 17 | 5 | 0.2 | 400 |

Stop time: 17 min
Post-run time: 10 min.

B FRET Enzyme Assay Protocol

Enzymatic activity was determined using a modification of the assay described by Taliani et al., [Taliani et al., Anal. Biochem., 240, pp. 60-67 (1996)]. An internally quenched fluorogenic peptide (FRET substrate), Ac-DED(EDANS) EEαAbuψ[COO]ASK (DABCYL)-NH2, was purchased from AnaSpec Incorporated (San Jose, Calif.). The assay was run in a continuous mode in a 96-well microtiter plate format. The buffer was composed of 50 mM HEPES (pH 7.8), 100 mM NaCl, 20% glycerol, 5 mM DTT, and 25 μM KK4A peptide (KKGSVVIVGRIVLSGK; SEQ ID NO:5). The KK4A peptide represents the central region of the NS4A cofactor from genotype 1a with lysine residues added for improved solubility [Landro et al. Biochemistry, 36, pp. 9340-9348 (1997)]. The reaction was initiated by the addition of the FRET substrate after a 10-min pre-incubation of the buffer components with 2 nM of the NS3 protease at room temperature. The reaction was monitored at 30° C. for 20 min using a Molecular Devices fmax fluorometric plate reader. The filters for excitation and emission wavelengths were 355 nm and 495 nm, respectively. For determination of substrate kinetic parameters, concentrations of the FRET peptide were varied from 0.5-7.0 μM. Inter-molecular quenching was not observed in this range. The substrate kinetic parameters, Km and Vmax, were determined by fitting the data to the Michaelis-Menten equation. Inhibition constants (Ki) were determined by titration of enzyme activity using the assay described above, except that compound dissolved in DMSO (no greater than 2% v/v DMSO; solvent only was used as control) was added to the buffer components and enzyme after the initial 10-min pre-incubation as described above. This mixture was incubated for an additional 15 min at room temperature prior to an incubation with the FRET substrate for another 20 min at 30° C. Seven to eight concentrations of compound were assayed, and the resulting data were fitted to the integrated form of Morrison's equation for tight binding inhibition [J. F. Morrison, Biochim. Biophys. Acta, 185 pp. 269-286 (1969)]. All substrate and inhibitor data were fitted using Marquardt-Levenberg nonlinear regression with GraphPad Prism software.

Example 8

Development of Resistance to VX-950 in HCV Replicon Cells

Figure 4:
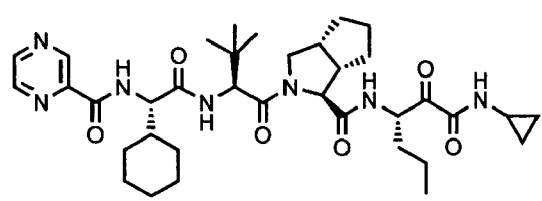
Figure 4:
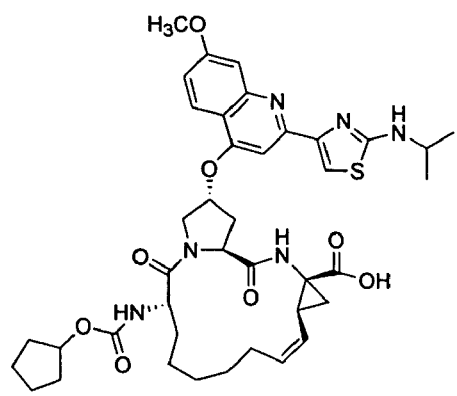

VX-950 (FIG. 4A, chemical structure) is a clinical candidate for Hepatitis C treatment. VX-950 is a reversible, covalent inhibitor of the HCV NS3•4A serine protease. Although competitive with the peptide substrate in the active site, it exhibits apparent non-competitive inhibition as a result of its tight binding properties and time dependent inhibition mechanism (C. Gates and Y-P. Luong). Incubation of the HCV Con1 sub-genomic replicon cells with VX-950 resulted in a concentration-dependent decline of the HCV RNA level, as measured by the real-time RT-PCR (Taqman) method (FIG. 5B). The IC50 value of VX-950 is 354 nM in the 48-hour assay.

Figure 5A:
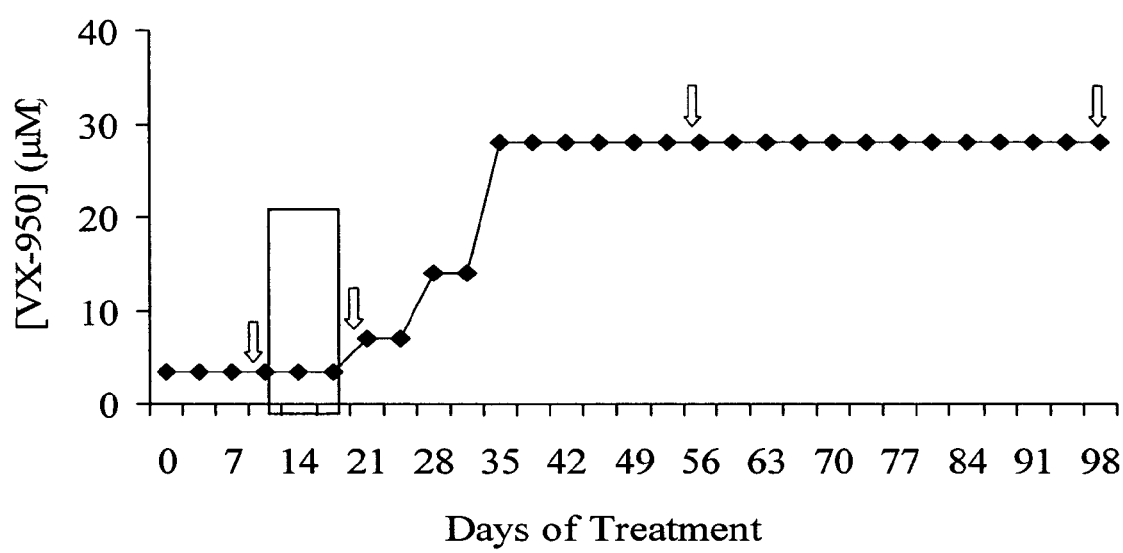
Figure 5B:
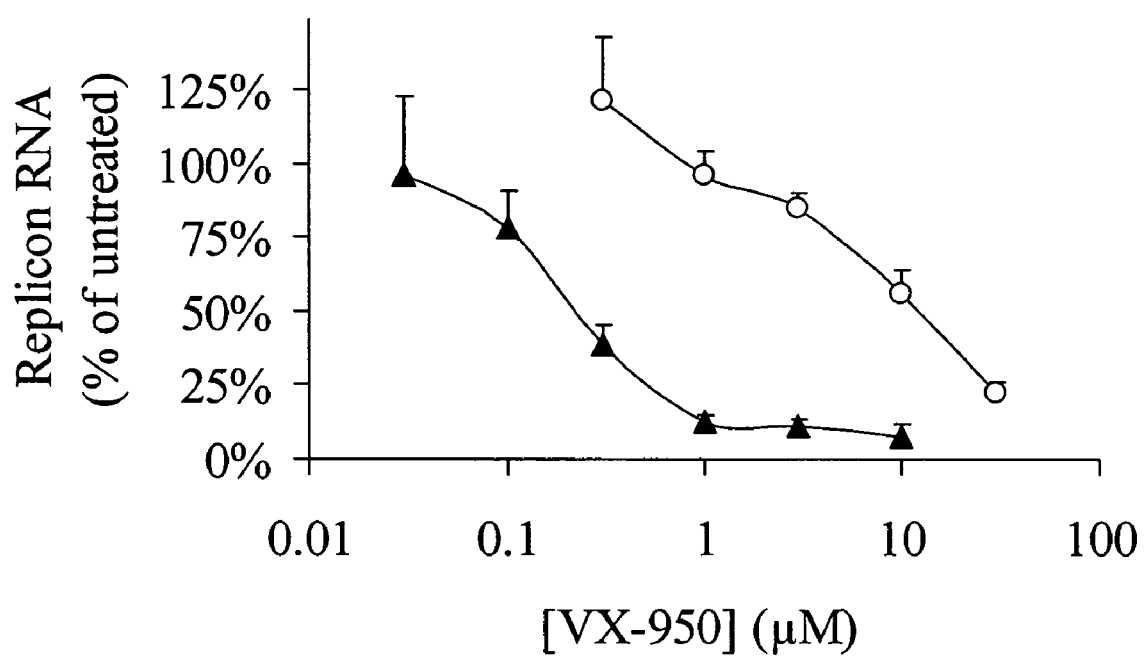

To identify VX-950 resistance mutations, the Con1 sub-genomic replicon cells were serially passaged (i.e., subcultured grown) in the presence of 0.25 mg per ml of G418 and gradually increasing concentrations of VX-950 (series A) (FIG. 5A, selection curve). The starting concentration of VX-950 was 3.5 μM or 10 times the IC50 and the highest concentration was 28 μM or 80 times of the IC50. Replicon cells were split or the medium was replenished every 3 or 4 days, and fresh VX-950 was added. Since VX-950 inhibits the HCV NS3 serine protease activity and consequently blocks replication of HCV RNA, the steady state level of HCV proteins and neomycin transferase protein gradually declined and eventually became undetectable in the presence of high concentration of VX-950. Cells with low or no neomycin transferase protein proliferate at a gradually decreasing rate and eventually die in the presence of G418. Only HCV RNA with mutations that are resistant to VX-950 can replicate in the presence of high concentration of VX-950 and support the growth of the replicon cells harboring them. Replicon cells in series A grew normally for the first 10 days in the presence of 3.5 μM VX-950. After 10 days, the series A cells grew significantly slower and massive cell death was observed between days 10 and 17 (FIG. 5A, selection curve). Normal growth did not resume until day 21. The IC50 of VX-950 against the series A replicon cells at day 56 was determined to be 8.1 to 12.0 μM, which is 23- to 34-fold higher than the IC50 (354 nM) against wild-type replicon cells (FIG. 5B, IC50 curve).

Total cellular RNAs from the series A cells at days 7, 21, and 56, were extracted and subjected to RT-PCR to amplify the coding region of the NS3 serine protease domain. The RT-PCR product was bulk-sequenced to identify the position(s) of potential mutations that could be responsible for the observed reduction in sensitivity to VX-950. The nucleotide and amino acid sequences of the wild-type HCV protease from the original replicon cells are shown in SEQ ID NO:1 and SEQ ID NO:2. No VX-950 related mutation was observed in the NS3 serine protease domain of the series A replicon cells at day 7 when compared to the wild type Con1 replicon cells cultured in the absence of VX-950.

At days 21 and 56 in series A, substitutions at Ala156 in the protease domain was observed, suggesting that mutations at residue 156 might be critical for the reduced sensitivity to VX-950. No mutation was found at any of the four proteolytic sites in the HCV nonstructural protein region that are cleaved by the NS3•4A serine protease. To delineate the identity and frequency of the substitutions, a 1.7-kb RT-PCR product of the series A replicon cells at day 7 or 98 was sub-cloned into the TA vector and multiple clones were sequenced for both samples. All clones derived from the day 7 samples contained the wild type Ala156. In the day 98 sample of the series A replicon cells, which had been cultured in the presence of 28 μM VX-950 for 63 days, 79% or 60 out of 76 clones had an alanine to serine (A156S) substitution.

In addition, VX-950 resistant cells have been selected under a constant concentration of VX-950 and G418. In this case, multiple colonies of resistant cells were observed after a prolonged culture period under VX-950 and G418. The HCV NS3 serine protease sequences were determined from these resistant colonies and the similar mutations at amino acid 156 of the HCV serine protease were found.

Example 9

Development of Resistance to BILN 2061 in HCV Replicon Cells

Figure 6A:
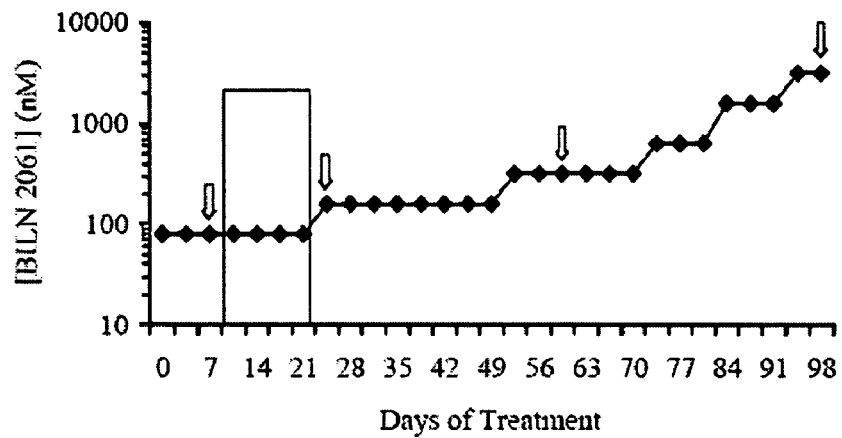
Figure 6B:
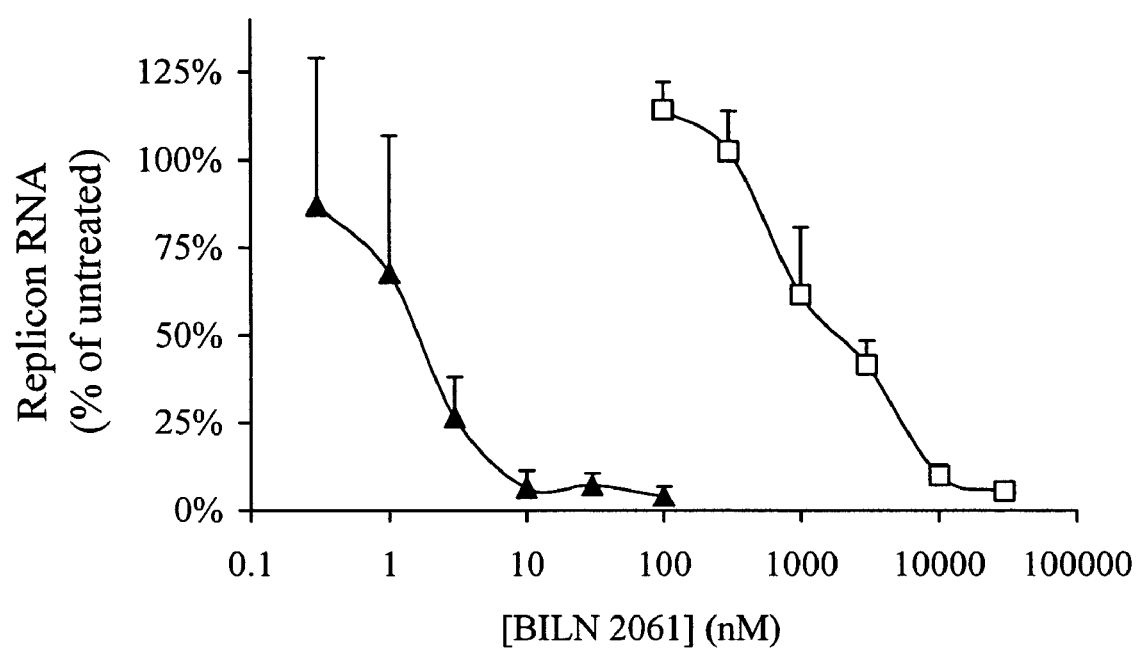

Another HCV NS3•4A protease inhibitor, BILN 2061 (FIG. 4B, chemical structure) (WO 00/59929; U.S. Pat. No. 6,608,027) has been demonstrated to be efficacious in Hepatitis C patients (Lamarre et al., Nature Medicine, 2003). HCV replicon cells resistant to BILN 2061 (series B) were selected in a similar manner as for VX-950. Again, wild-type Con1 sub-genomic HCV replicon cells were serially passed in the presence of 0.25 mg per ml of G418 and slowly increasing concentration of BILN 2061 (FIG. 6A, selection curve). Series B replicon cells grew normally for the first 7 days in the presence of 80 nM BILN 2061 or 80-fold above the IC50. However, the proliferation of series B cells slowed down significantly after day 7 and massive cell death was observed between days 7 and 17. As before, normal growth did not resume until day 21. BILN 2061 had an IC50 value of 1.0 to 1.8 µM against the series B cells at day 59, which is 1,000 to 1,800-fold higher than the IC50 (1 nM) against wild-type replicon cells (FIG. 6B, IC50 curve).

No BILN 2061 related mutation was observed in the NS3 serine protease domain at day 7. By day 24, a variety of substitutions were observed at amino acid 168 of the NS3 protein, suggesting that substitutions at residue 168 may account for the resistance against BILN 2061. No mutation at the four sites in the HCV nonstructural protein region that are cleaved by the NS3•4A serine protease was observed. To determine the frequency of various substitutions at the NS3 residue 168, the NS3 serine protease of the series B replicon at day 98, which was cultured in the presence of 3.2 µM BILN 2061, was sequenced. 60 out of 94 clones or 64% had an Asp168 to Val (D168V) substitution, and 23 clones or 24% had an Asp168 to Ala (D168A) mutation.

In addition, BILN 2061 resistant cells were selected under a constant concentration of BILN 2061 and G418. In this case, multiple colonies of resistant cells were observed after a prolonged culture period under BILN 2061 and G418. The HCV NS3 serine protease sequences were determined from these resistant colonies and the similar mutations at amino acid 168 of the HCV serine protease were found.

Example 10

Selection of Replicon Cells Resistant to Both VX-950 and BILN 2061

A. Development of Cross-Resistant HCV Replicons from VX-950-Resistant Cells

Figures 8A, 8B, 8C:
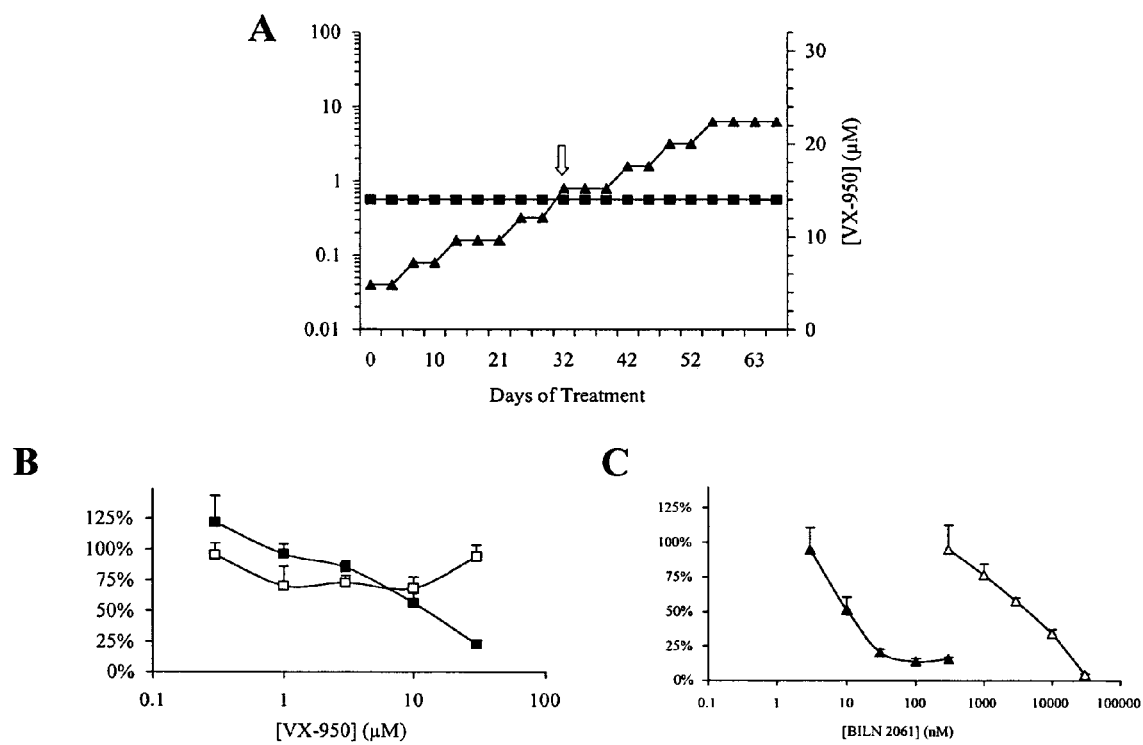

To identify resistance mutations that are cross-resistant to both VX-950 and BILN 2061, several schemes of selection were employed. First, a VX-950-resistant replicon cell line [series A in C. Lin et al. J. Biol. Chem. 279, pp. 17508-17514 (2004)] was serially passed in the presence of 0.25 mg/ml of G418, 14 µM VX-950, and slowly increasing concentrations of BILN 2061 (series C) (FIG. 8A). For BILN 2061, the starting concentration was 40 nM and the final concentration was 6.4 µM. Replicon cells were split or the medium was replenished every 3 or 4 days, and fresh VX-950 and BILN 2061 was added. Since HCV PIs inhibit the NS3•4A serine protease activity and consequently blocks replication of HCV RNA, the steady state level of HCV proteins and neomycin transferase protein gradually declined and eventually became undetectable in the presence of high concentration of HCV PI (data not shown). Cells with low or no neomycin transferase protein proliferate at a gradually decreasing rate and eventually die in the presence of G418. Replicon cells with the major VX-950-resistant mutation, A156S, are expected to die in presence of increasing concentrations of BILN 2061 since it has been shown to be susceptible to inhibition of BILN 2061 [C. Lin et al. J. Biol. Chem. 279, pp. 17508-17514 (2004)]. Only HCV RNA with mutations that are cross-resistant to both VX-950 and BILN 2061 can replicate in the presence of high concentrations of both HCV PIs and support the growth of the replicon cells harboring them. However, replicon cells in the series C grew normally for the entire selection process, which lasted for 56 days. The IC50 values of BILN 2061 against the series C replicon cells at day 52 were determined to be ~3 µM, which is 300-fold higher than the IC50 against the series A (VX-950-resistant) replicon cells (~10 nM) (FIG. 8B). Since 30 µM VX-950 did not resulted in more than 50% reduction of HCV RNA in the series C replicon cells at day 52, the actual IC50 values of VX-950 cannot be determined, which indicates the series C replicon cells at day 52 remain resistant to VX-950 (FIG. 8C).

Total cellular RNA from the series C cells at day 32, which had been cultured in the presence of 14 µM VX-950 and 0.32 µM of BILN 2061, was extracted and subjected to RT-PCR to amplify the coding region of the NS3 serine protease domain. The RT-PCR product was bulk-sequenced to identify the position(s) of potential mutations that could be responsible for the observed reduction in sensitivity to both HCV PIs. Substitutions at Ala156 in the protease domain were observed, suggesting that mutations at residue 156 might be critical for the reduced sensitivity to both PIs. This observation was somehow unexpected since the major VX-950-resistant mutation was found to be A156S [C. Lin et al. J. Biol. Chem. 279, 17508-17514 (2004)]. No mutation was found at any of the four proteolytic sites in the HCV nonstructural protein region that are cleaved by the NS3•4A serine protease. To delineate the identity and frequency of the substitutions, a 1.7-kb RT-PCR product of the series C replicon cells at day 32 was sub-cloned into the TA vector and 10 individual colonies were subjected to sequencing. 6 clones had an Ala156 to Thr (A156T) substitution, and 3 clones had a substitution of Ala156 with Val (A156V). The 10th clone retains the A156S mutation.

B. Development of Cross-Resistant HCV Replicons from BILN 2061-Resistant Cells

Figures 9A, 9B, 9C:
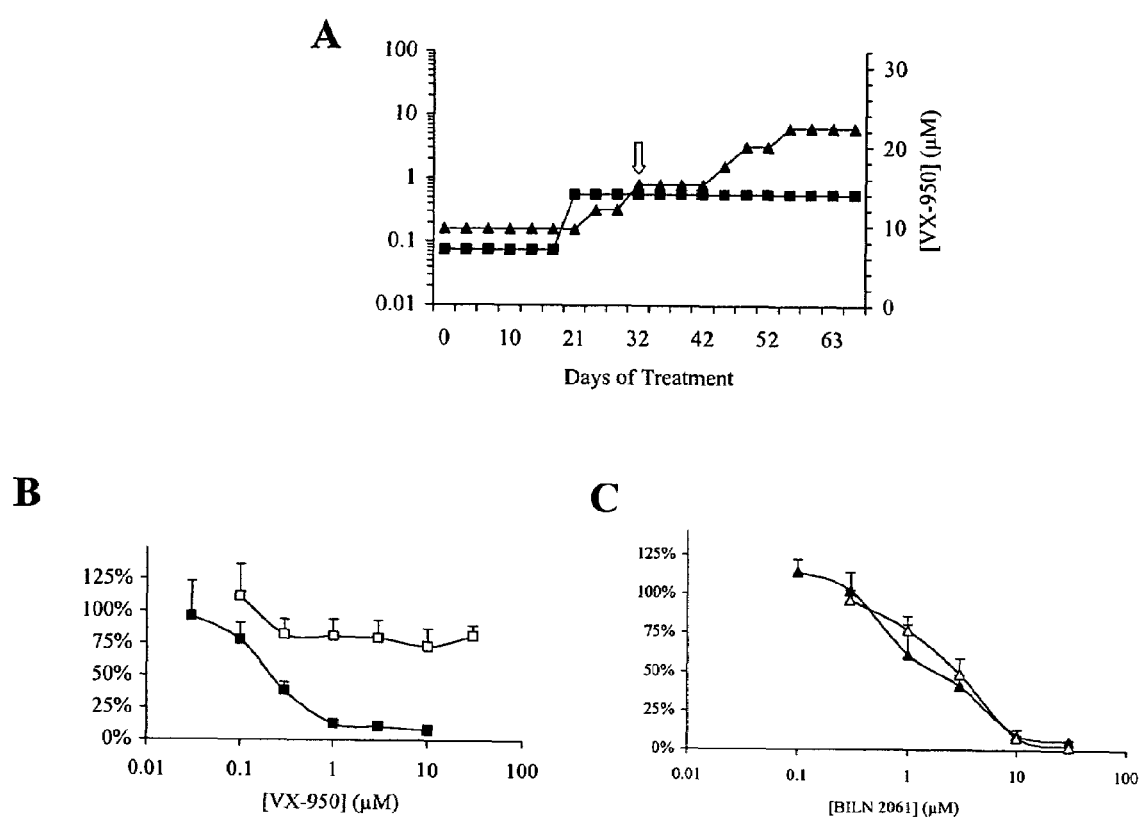
FIG. 9. Development of double-resistant replicons from BILN 2061-resistant replicon cells. (A) BILN 2061-resistant replicon cells were serially passed in the presence of 0.25 mg/ml G418, 7 or 14 µM VX-950 and increasing concentrations of BILN 2061. Replicon cells were split, and fresh VX-950 and BILN 2061 was added to medium twice a week, as indicated by filled rectangles and triangles, respectively. Total cellular RNA of replicon cells at day 32 during the resistance selection was extracted and the RT-PCR product covering the HCV NS3 serine protease was sequenced either directly or after being sub-cloned into the TA vector. (B) Titration of VX-950 against the series B (BILN 2061-resistant) (filled rectangle) or the series D (double-resistant) (open rectangle) replicon cells at day 52 by VX-950 was shown. HCV RNA level was determined after a 48-h incubation with VX-950. (C) Titration of BILN 2061 against the series B (BILN 2061-resistant) (filled triangle) or the series D (double-resistant) (open triangle) replicon cells at day 52 by BILN 2061 was shown HCV RNA level was determined after a 48-h incubation with BILN 2061.

The second selection scheme was to grow BILN 2061-resistant replicon cells in the presence of both BILN 2061 and VX-950. In this case, a BILN 2061-resistant replicon line [series B in C. Lin et al. J. Biol. Chem. 279, pp. 17508-17514 (2004)] was serially passed in the presence of 0.25 mg/ml of G418, and slowly increasing concentrations of VX-950 and BILN 2061 (series D) (FIG. 9A). For BILN 2061, the starting concentration was 160 nM and the final concentration was 6.4 µM. Only two concentrations of VX-950 were used: 7 µM and 14 µM. Replicon cells with the major BILN 2061-resistant mutations, D168V or D168A, are expected to die in presence of high concentrations of VX-950 since they have been shown to be susceptible to inhibition of VX-950 [C. Lin et al. J. Biol. Chem. 279, pp. 17508-17514 (2004)]. Again, only HCV RNA with mutations that are cross-resistant to both VX-950 and BILN 2061 can replicate in the presence of high concentrations of both HCV PIs and support the growth of the replicon cells harboring them. However, replicon cells in the series D grew normally for most of the selection process, which also lasted for 56 days. Since 30 μM VX-950 did not resulted in more than 50% reduction of HCV RNA in the series D replicon cells at day 52, the actual IC50 values of VX-950 cannot be determined, but it will be at least more than 100-fold higher than the IC50 (~0.3 μM) against the series B (BILN 2061-resistant) replicon cells (FIG. 9B). The IC50 values of BILN 2061 against the series D replicon cells at day 52 were determined to be ~4 μM, which indicates the series D replicon cells at day 52 remain resistant to BILN 2061 (FIG. 9C).

Total cellular RNA from the series D cells at day 32, which had also been cultured in the presence of 14 μM VX-950 and 0.32 μM of BILN 2061, was extracted and subjected to RT-PCR to amplify the coding region of the NS3 serine protease domain. The RT-PCR product was bulk-sequenced to identify the position(s) of potential mutations that could be responsible for the observed reduction in sensitivity to both HCV PIs. Again, substitutions at Ala156 in the protease domain were observed, confirming that mutations at residue 156 might be critical for the reduced sensitivity to both PIs. No mutation was found at any of the four proteolytic sites in the HCV nonstructural protein region that are cleaved by the NS3•4A serine protease. To delineate the identity and frequency of the substitutions, a 1.7-kb RT-PCR product of the series A replicon cells at day 32 was sub-cloned into the TA vector and 14 individual colonies were subjected to sequencing. 12 clones had the A156V substitution, while 1 clone had the A156T mutation. The 14th clone has two mutations, A156S and D168V.

C Development of Cross-Resistant HCV Replicons from Naïve Replicon Cells

In our previous studies of resistance mutations against a single HCV PI, either VX-950 or BILN 2061, cell growth was stalled for several days, during which massive cell death was observed [C. Lin et al. J. Biol. Chem. 279, pp. 17508-17514 (2004)], which signaled the emergence of resistance mutant replicon cells and concurrent death of non-resistance replicons. However, no such cell death or slowdown in cell growth was observed in selection of the cross-resistant replicon series C or D as described above. It is possible that the cross-resistance mutations, A156T and A156V, may have already existed in VX-950—(series A) or BILN 2061—(series B) resistant replicon cells as a minor population. If so, these two selection schemes could provide bias toward the A156T or A156V mutation over other potential cross-resistance mutations. Thus, a third selection scheme was performed using the naïve HCV replicon cells that are sensitive to either inhibitor.

Figure 10:
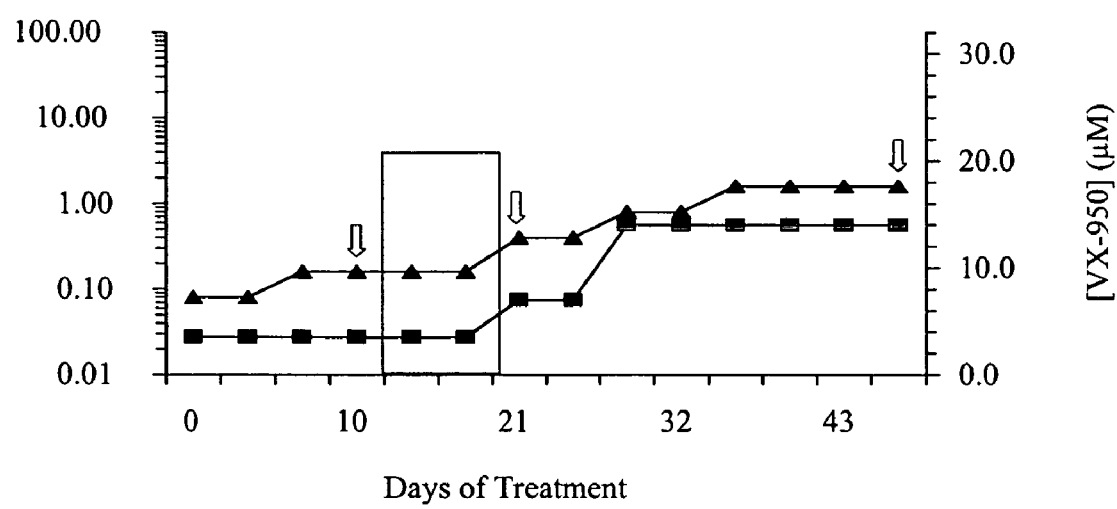
FIG. 10. Development of double-resistant replicons from naive replicon cells. HCV subgenomic replicon cells were serially passed in the presence of 0.25 mg/ml G418, and increasing concentrations of VX-950 and BILN 2061. Replicon cells were split, and fresh VX-950 and BILN 2061 was added to medium twice a week, as indicated by filled rectangles and diamonds, respectively. The boxed area indicates the time period in which the replicon cells had little or no overall growth accompanied by a concurrent massive cell death. Total cellular RNA of replicon cells at various time points, indicated by open arrows, during the resistance selection was extracted and the RT-PCR product covering the HCV NS3 serine protease was sequenced either directly or after being sub-cloned into the TA vector.

The Con1 subgenomic replicon cells driven from pBR322-HCV-Neo-mADE [C. Lin et al. J. Biol. Chem. 279, pp. 17508-17514 (2004)] were serially passed in the presence of 0.25 mg/ml of G418 and slowly increasing concentrations of both VX-950 and BILN 2061 (series E) (FIG. 10). The starting concentration of VX-950 was 3.5 μM and the highest concentration was 14 μM. For BILN 2061, the starting concentration was 80 nM and the final concentration was 3.2 μM. Replicon cells were split or the medium was replenished every 3 or 4 days, and fresh VX-950 and BILN 2061 was added. Replicon cells in series E grew normally for the first 10 days in the presence of 3.5 μM VX-950 and 160 nM BILN 2061. After 10 days, the series E cells grew significantly slower and massive cell death was observed between days 10 and 21 (FIG. 10). Normal growth did not resume until day 21. Total cellular RNA from the series C cells at days 10, 21, and 48, were extracted and subjected to RT-PCR to amplify the coding region of the NS3 serine protease domain. No HCV PI-related mutation was observed in the NS3 serine protease domain of the series E replicon cells at day 10 when compared to the wild type Con1 replicon cells cultured in the absence of both HCV PIs. To delineate the identity and frequency of the substitutions, a 1.7-kb RT-PCR product of the series E replicon cells at day 21 or 48 was sub-cloned into the TA vector and multiple clones were sequenced for both samples. In the day 21 sample of the series E replicon cells, which had been cultured in the presence of 3.5 μM VX-950 and 0.32 μM of BILN 2061 for 14 days, 65% or 30 out of 46 clones had an Ala156 to Thr (A156T) substitution, while another substitution of Ala156 with Val (A156V) was found in 35% or 16 out of 46 clones. For the day 48 sample of the series E, which had been cultured in the presence of 14 μM VX-950 and 1.6 μM of BILN 2061 for 14 days, 80% or 35 out of 44 clones had the A156T substitution, while the A156V substitution was found in 20% or 9 out of 44 clones. In either case, no other mutations in the NS3 serine protease domain was found in more than 10% of the TA plasmid clones, indicating that A156T and A156V are only two mutations that confer cross-resistance to both VX-950 and BILN 2061.

Example 11

Demonstration and Confirmation of Resistant Mutations at Amino Acid 156 or 168 in the Enzymatic and Replicon Cell Assays To confirm whether the observed mutations at either Ala156 or Asp168 are sufficient to confer resistance against VX-950 or BILN 2061, respectively, site-directed mutagenesis was used to introduce each individual mutation at position 156 or 168 into the wild type NS3 protease domain.

Site-specific mutagenesis is another technique useful in the preparation of the mutant protease proteins used in the methods of the invention. This technique employs specific mutagenesis of the underlying DNA (that encodes the amino acid sequence that is targeted for modification). The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids also are routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization (annealing) conditions, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

Of course, the above described approach for site-directed mutagenesis is not the only method of generating potentially useful mutant protease species and as such is not meant to be limiting. The present invention also contemplates other methods of achieving mutagenesis such as for example, treating the recombinant vectors carrying the gene of interest mutagenic agents, such as hydroxylamine, to obtain sequence variants.

A. The Dominant VX-950 Resistant Mutant, A156S, Remains Susceptible to BILN 2061

To confirm whether the observed substitution of Ala156 with Ser are sufficient to confer resistance against VX-950 but not BILN 2061, site-directed mutagenesis was used to replace Ala156 with Ser in the wild type NS3 protease domain.

The kinetic parameters for the FRET substrate for the wild type NS3 protease domains from genotype 1a and 1b were identical (Table 1) under our assay conditions. Although the NS4A peptide co-factor was from HCV genotype 1a, no discernable difference in the kinetic parameters was observed. This is consistent with molecular modeling, which suggests that the conservative variations in the central region of NS4A between genotypes 1a and 1b do not affect the interaction between the NS4A core peptide and the NS3 protease domain. Ki values of VX-950 and BILN 2061 were determined using genotypes 1a and 1b wild type protease, and there were no statistically significant differences between the two wild type proteases (Table 2).

The kinetic parameters of the FRET substrate for the A156S mutant protease were virtually the same as that of the wild type protease (Table 1). However, the Ki value of VX-950 was 2.9 μM against the A156S mutant protease, which is 29-fold higher than that against the wild type protease (0.1 μM) (Table 2). BILN 2061 had a Ki value of 112 nM against the A156S mutant, which was 6-fold higher than that against the wild type protease, 19 nM (Table 2).

The HCV RNA level in the replicon cells containing the A156S substitution was similar to that of wild type replicon cells (data not shown), which is consistent with the similar enzymatic catalytic efficiency of the A156S mutant and the wild type NS3 serine proteases. The IC50 value of VX-950 against the A156S replicon cells was 4.65 μM, which is 12 times higher than that against the wild type replicon cells (0.40 μM) (Table 3). The difference between the IC50 values of BILN 2061 against the A156S (7 nM) and the wild type replicon (4 nM) cells was not significant (Table 3).

B The Major BILN 2061 Resistant Mutants, D168V and D168A, Remain Fully Susceptible to VX-950

To confirm whether the observed substitution of Asp168 with Val or Ala are sufficient to confer resistance against BILN 2061 but not VX-950, site-directed mutagenesis was used to replace Asp168 with either Val or Ala in the wild type NS3 protease domain.

The substrate kinetic parameters were not affected by the D168V mutation, and showed only minor changes (less than 10-fold) for the D168A mutant as indicated by the comparison of the kcat and kcat/Km values of the wild type and the two mutant NS3 serine proteases (Table 1). Similarly, no significant effect of either substitution at Asp168 was observed on the Ki value of VX-950 (Table 2). However, the substitution of valine or alanine for aspartic acid at position 168 resulted in a mutant NS3 protease that was not inhibited by up to 1.2 μM BILN 2061 (Table 2). These data indicate that either mutant protease is at least 63-fold less susceptible to BILN 2061 as compared to the wild type protease. The actual magnitude of resistance cannot be determined since BILN 2061 was not soluble at concentrations greater than 1.2 μM in the assay buffer, as measured by the absorbance at 650 nm. The D168V or D168A mutation was also introduced into the wild type HCV replicon by site-directed mutagenesis and a stable replicon cell line carrying either substitution was generated. BILN 2061 had an IC50 of 5.09 μM against the D168V replicon cells, which is more than 1,300 times higher than against wild type replicon cells (4 nM) (Table 3). The IC50 of BILN 2061 was 1.86 μM against the D168A mutant replicon. There was little change in IC50 values of VX-950 against the D168V and the wild type replicon cells (Table 3).

Table 1 shows characterization of enzymatic properties of the wild type or the mutant HCV NS3 serine protease domains. Five HCV NS3 serine protease domain proteins, including the genotype 1a and 1b wild-type (wt) proteases, and three mutants (A156S, D168V, and D168A) of the genotype 1b, were expressed and purified as described in Materials and Methods. The kcat and Km values of these NS3 proteases were determined using the KK-NS4A core peptide and the FRET substrate.

TABLE 1 enzymatic characterization of wild type or mutant HCV NS3 serine proteases

| HCV Protease | Km (μM) | Kcat ($^{s-1}$) | Kcat/Km ($M^{-1}s^{-1}$) |
|---|---|---|---|
| Wt (1a) | 1.3 | 1.2 | $8.97 \times 10^5$ |
| Wt (1b) | 1.1 | 1.0 | $9.47 \times 10^5$ |
| A156S (1b) | 0.9 | 0.6 | $6.64 \times 10^5$ |
| D168V (1b) | 1.2 | 0.6 | $4.98 \times 10^5$ |
| D168A (1b) | 2.0 | 0.3 | $1.50 \times 10^5$ |

Table 2 shows confirmation of resistance in enzymatic assay. The Ki values of VX-950 and BILN 2061 were determined against the five purified HCV NS3 serine protease domains, including the wild type (wt) proteases from genotype 1a or 1b, as well as three mutants, A156S, D168V, and D168A in genotype 1b, using the KK-NS4A peptide and the FRET substrate. The solubility of BILN 2061 in the reaction buffer was limited at concentrations above 1.2 μM. No inhibition was observed for either D168V or D168A mutant NS3 protease in the presence of 1.2 μM BILN 2061.

TABLE 2

Ki Values of VX-950 and BILN 2061 against wild-type and mutant NS3 proteases

| | Ki (μM) | |
|---|---|---|
| Mutant | BILN 2061 | VX-950 |
| Wt (1a) | 0.006 | 0.047 |
| Wt (1b) | 0.019 | 0.100 |
| A156S | 0.112 | 2.9 |

TABLE 2-continued Ki Values of VX-950 and BILN 2061 against
wild-type and mutant NS3 proteases

| | Ki (µM) | |
|---|---|---|
| Mutant | BILN 2061 | VX-950 |
| D168V | >1.2 | 0.043 |
| D168A | >1.2 | 0.150 |

Table 3 shows confirmation of resistance in HCV replicons. Four HCV sub-genomic replicon stable cell lines, including the wild type (wt), and three mutants, A156S, D168V and D168A, were generated using the T7 RNA runoff transcripts from the corresponding high efficiency Con1 replicon plasmids. The IC50 values of VX-950 and BILN 2061 were determined against the four HCV replicon cell lines in the standard 48-hour assay.

TABLE 3

$IC_{50}$ values of VX-950 and BILN 2061 against the HCV replicon
cells with the wild-type and mutant NS3 proteases

| | Replicon $IC_{50}$ (µM) | |
|---|---|---|
| Mutant | BILN 2061 | VX-950 |
| Wt | 0.004 | 0.402 |
| A156S | 0.007 | 5.09 |
| D168V | 4.65 | 0.163 |
| D168A | 1.86 | 0.193 |

C. The A156T and A156V Mutations are Cross-Resistant to Both VX-950 and BILN 2061

To confirm whether the observed mutations at Ala156 are sufficient to confer cross-resistance against both VX-950 and BILN 2061, site-directed mutagenesis was used to replace Ala156 with either Val or Thr in the wild type NS3 protease domain.

The catalytic efficiency (kcat/Km) of A156T or A156V mutant protease against the FRET substrate were about 5 to 7-fold lower than that of the wild type protease (Table 4). The Ki value of VX-950 was 9.9 µM or 33 µM against the A156T or A156V mutant protease, respectively, which is 99- or 330-fold higher than that against the wild type protease (0.1 µM), respectively (Table 5). Either mutant protease was not inhibited by up to 1.2 µM BILN 2061 (Table 5). These data indicate that either mutant protease is at least 63-fold less susceptible to BILN 2061 as compared to the wild type protease. The actual magnitude of resistance cannot be determined since BILN 2061 was not soluble at concentrations greater than 1.2 µM in the assay buffer, as measured by the absorbance at 650 nm (data not shown).

TABLE 4

Enzymatic properties of the wild type or the
mutant HCV NS3 serine protease domains

| HCV Protease | Km (µM) | kcat (s − 1) | kcat/Km (M − 1 s − 1) |
|---|---|---|---|
| Wild-type | 1.1 | 1.0 | $9.47 \times 10^5$ |
| A156T | 1.3 | 0.2 | $1.36 \times 10^5$ |
| A156V | 2.6 | 0.6 | $2.34 \times 10^5$ |

Table 4 summary: Three HCV NS3 serine protease domain proteins of the Con1 strain, including the wild-type proteases and two mutants, A156T and A156V, were expressed and purified. The kcat and Km values of these NS3 proteases were determined using the KK-NS4A core peptide and the FRET substrate, and the average of two independent assays was shown.

TABLE 5

Confirmation of resistance in enzymatic assay

| | Ki (µM) | |
|---|---|---|
| Mutant | BILN 2061 | VX-950 |
| Wild-type | 0.019 | 0.100 |
| A156T$_{(n=2)}$ | >1.2 | 9.9 |
| A156V$_{(n=1)}$ | >1.2 | 33 |

Table 5 summary: The Ki values of VX-950 and BILN 2061 were determined against the five purified HCV NS3 serine protease domains, including the wild-type protease, as well as two mutants, A156T and A156V, using the KK-NS4A peptide and the FRET substrate. The solubility of BILN 2061 in the reaction buffer was limited at concentrations above 1.2 µM. No inhibition was observed for either A156T or A156V mutant NS3 protease in the presence of 1.2 µM BILN 2061.

The HCV RNA level in the replicon cells containing the A156T or A156V substitution was lower than that of wild type replicon cells (data not shown), which is consistent with the lower enzymatic catalytic efficiency of the two mutant as compared to that of the wild type NS3 serine proteases. No significant reduction of HCV replicon RNA by up to 30 µM VX-950 was observed in either mutant replicon cell line, indicating at least 75-fold decrease in sensitivity conferred by either mutation (Table 6). The IC50 value of BILN 2061 against either A156T replicon cells was 1.09 µM, which is about 272-times higher than that against the wild type replicon cells (4 nM). For the A156V mutant replicons, BILN 2061 has an IC50 value of 5.76 µM, indicating a more than 1,400-fold decrease in sensitivity conferred by A156V mutation (Table 6).

TABLE 6

Confirmation of resistance in HCV replicons

| | Replicon $IC_{50}$ (µM) | |
|---|---|---|
| Mutant | BILN 2061 | VX-950 |
| Wild-type | 0.004 | 0.402 |
| A156T | 1.09 | >30 |
| A156V | 5.76 | >30 |

Table 6 summary: Three HCV sub-genomic replicon stable cell lines, including the wild-type, and two mutants, A156T and A156V, were generated using the T7 RNA runoff transcripts from the corresponding high efficiency Con1 replicon plasmids. The IC50 values of VX-950 and BILN 2061 were determined against the three HCV replicon cell lines in the standard 48-hour assay, and the average of two independent assays was shown.

Example 12

Modeling—I

VX-950 and BILN 2061 were modeled into the active site of the NS3 serine protease domain using the structure of the full-length HCV NS3 protein published by Yao et al., [Yao., et al., Structure Fold Des., 7, pp. 1353-1363 (1999)] (PDB code: 1CU1). The coordinates of the protease domain of the A segment in this structure showed that the C-terminal strand of the NS3 protein binds in the substrate-binding site of the protease. The terminal carboxyl group of this strand is located near active site residues His57, Asp81, and Ser139 such that it forms hydrogen bonds with the side-chains of His57 and Ser139 as well as the backbone amides of residues 137 and 139, which form the oxyanion hole. Additionally, the last six residues (626 to 631) of the NS3 protein form an extended, anti-parallel β strand along the edge of the E2 strand of the protease β barrel and makes twelve backbone-to-backbone hydrogen bonds. A product-based inhibitor like BILN 2061 is expected to bind the NS3 protease in a similar fashion. Therefore, we utilized the coordinates of this crystal structure to build our models of inhibitor-protease co-complexes. BILN 2061 molecule was built in QUANTA molecular modeling software (Accelrys Inc., San Diego, Calif., USA), and manually docked into the active site such that its carboxyl group overlays with the NS3 C-terminal carboxylate of the full-length NS3 protein. The inhibitor molecule was then rotated such that it made all the following backbone hydrogen bonds: P1 NH with Arg155 carbonyl, P3 carbonyl with Ala157 NH, and P3 NH with Ala155 carbonyl. This mode of binding placed the large P2 group of BILN 2061 in direct clash with the Arg155 side-chain. To avoid the clash, the Arg155 side-chain was modeled in an extended conformation as suggested by the description of the crystal structure of an NS3 protease complex with a inhibitor which is analogous to BILN 2061 [Y. S. Tsantrizos, Angew. Chem. Int. Ed. Engl. 42, pp. 1356-1360 (2003)]. The inhibitor was energy minimized in two stages. In the first stage, only the inhibitor and the side-chain atoms of Arg155, Asp168 and Arg123 of the protease were allowed to move during energy minimization for 1000 steps. In the second stage, all the side-chain atoms of the active site were allowed to move along with the inhibitor for 1000 additional steps. This modeled structure closely mimics the published structure of the BILN 2061 analog [Y. S. Tsantrizos, Angew. Chem. Int. Ed. Engl. 42, pp. 1356-1360 (2003)].

A similar procedure was adopted for modeling VX-950 into the protease active site. The inhibitor was modeled as a covalent adduct with si-face attachment of the Ser139 side-chain to the keto carbonyl of the inhibitor. This binding mode has been observed for analogous ketoamide inhibitors [Perni et al., Bioorg. Med. Chem. Lett. 14, in press (2004)] and ketoacid inhibitors [Di Marco et al., J. Biol. Chem., 275, pp. 7152-7157 (2000)]. The main-chain of the inhibitor was overlaid with the residues 626 to 631 of the NS3 C-terminal strand such that it made all the following backbone hydrogen bonds: P1 NH with Arg155 carbonyl, P3 carbonyl with Ala157 NH, P3 NH with Ala157 carbonyl, and the P4 cap carbonyl with the NH of Cys159. In this binding mode, the P2 group of VX-950 was placed in the S2 pocket without any need to move the Arg155 side-chain. The t-butyl and the cyclohexyl groups were placed in S3 and S4 pockets, respectively. To be consistent, we used the same two-stage energy minimization protocol used for the BILN 2061 model. These two co-complex models were used to predict the effect of mutations at Ala156 and Asp168 on binding of the protease inhibitors.

The side-chain of Asp168 is exposed to solvent. The valine side-chain of the D168V mutant can adopt three canonical conformations with $\chi_1$=60°, –60° or 180°. All the three orientations of Val168 side-chain were modeled. The interaction energy of the D168V mutant enzyme and the inhibitor was minimized by allowing the inhibitor and Val168 atoms to move while fixing positions of all the other atoms of the protein molecule. In all cases, the Val168 side-chain does not cause any steric clash with the inhibitor atoms. The serine mutation at Ala156 was modeled by the following procedure. Ala156 side-chain is in van der Waals contact with the P2 group of both the inhibitors (FIG. 9). The serine side-chain of the A156S mutant was modeled at three canonical conformations of $\chi_1$=60°, –60° and 180°, and the energy was minimized by holding the conformation of the rest of the protein fixed. These models were used to examine the effects of this mutation on inhibitor binding. The –60° conformation was found to have the lowest energy as it forms a hydrogen bond with the neighboring Arg155 carbonyl, but it causes the maximal number of unfavorable contacts with both inhibitors. The 60° and 180° conformations are energetically equivalent, but the 60° conformation has fewer unfavorable contacts and was used in our analysis.

Ala156 is located on the E2 strand in the HCV NS3•4A protease structure [R. A. Love at al, Cell 87, pp. 331-342 (1996)]. Several backbone atoms of this strand (mainly the carbonyl of Arg155 and both the main-chain nitrogen and carbonyl of Ala157) make hydrogen bonds with the backbone atoms of substrates or substrate-based inhibitors. In our structural model of the VX-950:NS3 protease co-complex (FIG. 9), three hydrogen bonds are formed between P1 NH and Arg155 carbonyl, P3 carbonyl and Ala157 NH, and P3 NH and Ala157 carbonyl. The same hydrogen bonds are also formed in the co-complex model of BILN 2061. The Ala156 side-chain is in van der Waals contact with the P2 group of these inhibitors. In our A156S mutant model, the terminal oxygen of Ser156 is too close to the P4 cyclohexyl group of VX-950, and it is also close to the terminal cyclopentyl cap of BILN 2061. Since the cyclopentyl cap of BILN 2061 is at the flexible end of the inhibitor, it can be moved away from this unfavorable contact without losing much of the binding. A similar movement of the P4 cyclohexyl group of VX-950 causes destabilization of the interactions between the inhibitor and S4 and S5 sub-sites of the protease. Therefore, a larger loss in binding is expected for VX-950 than for BILN 2061 with the A156S mutant protease.

Asp168 is located in the F2 strand of the NS3 protease structure and is involved in salt-bridge interactions with the side-chains of Arg123 and Arg155 (FIG. 9) [R. A. Love at al, Cell 87, pp. 331-342 (1996)]. It is also part of the S4 binding pocket. The aliphatic part of this side-chain is in van der Waals contact with the terminal cyclopentyl group of BILN 2061, which is not expected to be affected by the D168V mutation, since a valine side-chain at this position does not cause any steric clash with the inhibitor. However, this D168V substitution results in the loss of salt-bridge interaction with the Arg155 side-chain on the neighboring E-2 strand (FIG. 1), which in turn makes multiple contacts with the large P2 group of BILN 2061 in the model described here. The conformation of the Arg155 (FIG. 9, color coded in cyan) in the model of the BILN 2061 wild type NS3 protease complex is no longer energetically favored in the D168V mutant for two reasons. First, it cannot remain close to the backbones of the E-2 strand in the absence of the salt-bridge interaction between Arg155 and Asp168. Second, an uncompensated and solvent-exposed positive charge of Arg155 side-chain will seek a larger solvation shell, as observed in the crystal structures of the apo-protease and the two protease:inhibitor complexes that are available in the Protein Data Bank (code: 1DY8 and 1DY9) [S. Di Marco et al., J. Biol. Chem., 275 pp. 7152-7157 (2000)]. These conformation of Arg155 are in direct clash with the P2 quinoline group of BILN 2061 and destabilize its binding. Therefore, substitution of Asp168 with any amino acid, other than glutamate, will disrupt the salt-bridge interactions with Arg155 and result in reduction of BILN 2061 binding. On the other hand, the conformation of Arg155 in the two published crystal structures of the NS3 protease:inhibitor complex is similar to that in our VX-950: protease complex model (color coded in orange in FIG. 9). In addition, this conformation of Arg155 confers stabilization of VX-950 binding as it allows the maximal number of van der Waals contacts between the Arg155 side-chain and the inhibitor. Therefore, VX-950 is not expected to be affected by the substitutions at Asp168 as compared to BILN 2061.

Example 13

Modeling—II

Figure 7:
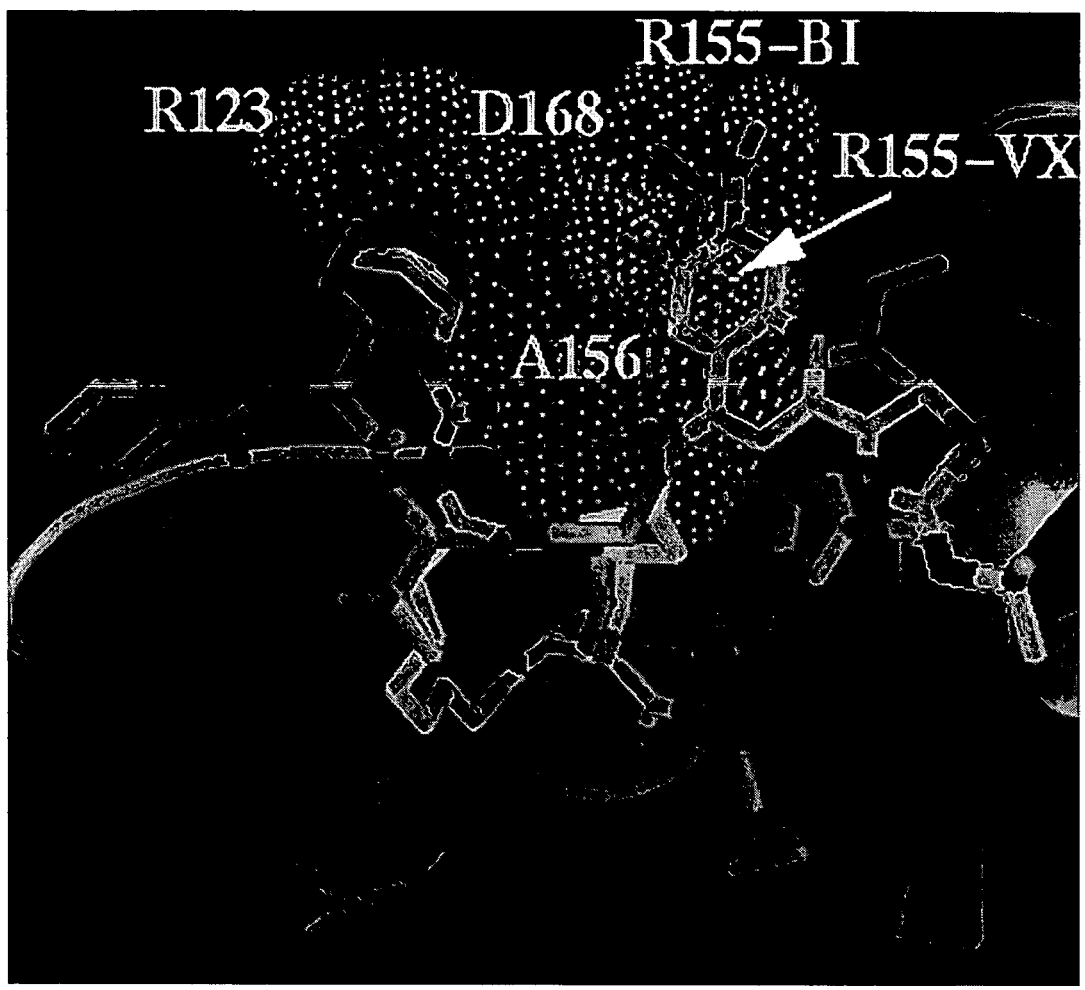

Modeling of VX-950 and BILN 2061 into the active site of the NS3 serine protease domain using the crystal structure of the a full-length HCV NS3 protein [N. Yao et al., Structure Fold Des. 7, pp. 1353-1363 (1999)] (Protein Data Base code: 1CU1) was previously described [C. Lin et al. J. Biol. Chem. 279, 17508-17514 (2004)]. The Ala156 side chain on the E2 β-strand of the HCV NS3•4A protease separates the S4 and S2 pockets of the enzyme active site and is in van der Waals contact with the P2 group of the two inhibitors (FIG. 7). The Val or Thr substitution of Ala156 extends the side chain with two additional (methyl or hydroxyl) groups into the compact space between the wild type enzyme and the inhibitors. The Val156 or Thr156 side chain was modeled at all the three possible canonical conformations of $\chi_1$=60°, −60° and 180° following the procedure outlined previously for the modeling of A156S mutation [C. Lin et al., J. Biol. Chem., 279 pp. 17508-17514 (2004)]. The side chain conformations were energy-minimized by holding the conformation of the rest of the protein fixed. The inhibitors, VX-950 and BILN 2061, were docked into these mutant enzyme active sites to elucidate the effect of the mutations on inhibitor binding.

Figure 11:
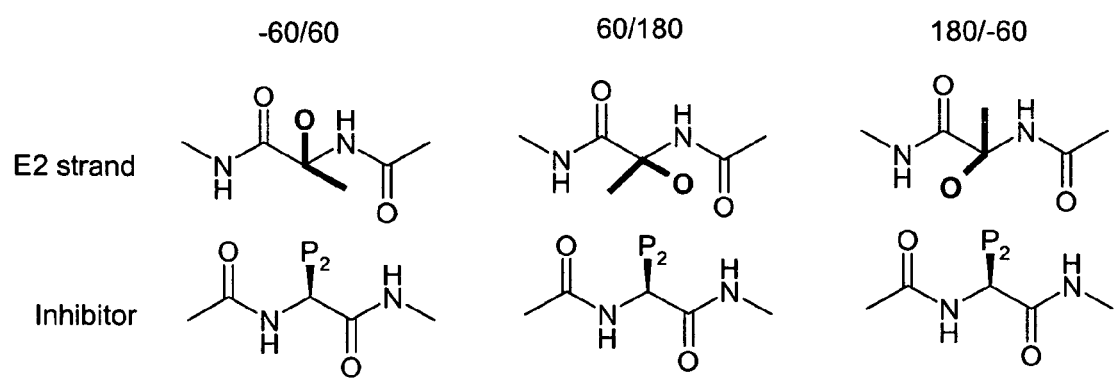
FIG. 11. The schematics of the Thr156 side chain conformations in relationship to the inhibitor binding. The thick lines represent the side chain of Thr156 of the mutant enzyme and the P2 side chain of the inhibitor or substrate. The same three conformations were also considered for Val156 side chain. The last (−60/180°) conformations has the lowest energy for either mutation, but remains repulsive to both the inhibitors.

Of the three possible conformations of the Ser side chain at position 156 (FIG. 11), the conformation with $\chi_1$=60° has the least number of unfavorable contacts with VX-950 and BILN 2061. The other two conformers (with $\chi_1$=180° and −60°) have multiple unfavorable contacts with both the inhibitors either at the P2 side chain or P3 carbonyl group. In A156T or A156V mutation, the additional group at the Cβ atom of the side chain is forced to occupy one of these two positions with $\chi_1$=180° or −60°, which makes unfavorable interactions with the inhibitors. The three possible conformations of Thr are shown schematically in FIG. 11. In all cases, the additional group has repulsive interaction with the inhibitor and/or enzyme backbone atoms. By energy minimization, we found that −60/180° conformation has the least repulsive interaction and main cause of the repulsion is the close clash between terminal methyl or hydroxyl group of the mutant side chain and P3 carbonyl group of the inhibitors. Therefore, A156T and A156V mutations are resistant to both the inhibitors.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference. The following list of references cited herein throughout are specifically incorporated herein by reference.

Alter, H. J., and Seeff, L. B. (2000) Semin. Liver Dis. 20, 17-35.
Alter, M. A. (1997) Hepatology 26:62. (disease)
Babine, R. E., et al. (2002) in WO 0218369, Eli Lilly and Company
Barbato et al., (1999) J. Mol. Biol. 289: 371-384 (NMR struture of NS3-4A protease)
Bartenschlager, R., et al. (1993) J. Virol. 67, 3835-3844
Bartenschlager, R., et al. (1995) J. Virol. 69, 7519-7528
Bartenschlager, R., et al., (1993) J. Virol. 3835-3844 (NS3 serine protease)
Beaulieu, P.-L. & M. Llinas-Brunet (2002) Curr. Med. Chem. 1: 163-176 (HCV NS target therapy)
Behrens, S. E. et al., (1996) EMBO J. 15: 12-22 (NS5B polymerase)
Benhamou, Y. et al., (2002) Hepatology, 36 (4), p. 106A.
Benhamou, Y., et al., (2002) Hepatology 36 (4) Abst. 463 (BILN 2061 clinical)
Beyer, B. M., et al. (2001) Proteins 43: 82-88. (GT3)
Blight, et al (2000) Science 290: 1972-1974. (adaptive)
Blight, K. J., et al. (1998) Antiviral Ther. 3, Suppl. 3, 71-81
Blight, K. J., et al. (2000) Science 290, 1972-1974.
Chander, G., et al., (2002) Hepatology 36: S135-144 (HCV treatment review)
Choo, Q. L. (1989) Science 244: 359-362 (discovery of HCV sequences)
Davies, G. L., et al., (1998) N. Eng. J. Med 339: 1493-1499 (pegIFN+RBV)
De Francesco, R. et al. (2003) Antiviral Res. 58, 1-16. (HCV NS inhibitor review)
De Francesco, R. and C. Steinkuhler (2000) Curr. Top. Micriobiol. Immunol. 242: 149-169 (HCV NS3-4A protease review on structure and function)
Di Marco, S., et al., (2000) J. Biol. Chem 275: 7152-7157 (PI co-structure)
Failla, C., et al. (1995) J. Virol. 69, 1769-1777
Frese, M., et al., (2001) J. Gen. Virol. 82: 723-733.
Grakoui, A., et al. (1993) J. Virol. 67, 1385-1395
Grakoui, A., et al., (1993) J. Virol. 67: 2832-2843 (NS3 serine protease)
Grakoui, A., et al., (1993) Proc. Natl. Acad. Sci. USA 90: 10583-10587 (NS2-3 auto-protease)
Hijikata, M., et al. (1993) Proc. Natl. Acad. Sci. USA 90, 10773-10777
Hijikata, M., et al., (1993) J. Virol. 67: 4665-4675 (two HCV proteases)
Hinrichsen, H. et al., Hepatology 2002, 36 (4), p. 145A
Hinrichsen, H., et al., (2002) Hepatology 36 (4) Abst. 866. (BILN 2061 clinical)
Hirsch, M. S., et al. (2003) Clin. Infect. Dis. 37, 113-128.
Houghton, M. (1996) Field Virology book, pp. 1035-1058
Kenny-Walsh, E., (2001) Clin. Liver Dis. 5: 969-977 (HepC natural history)
Kim, D. W., et al., (1995) Bichim Biophys. Res. Corn. 215: 160-166 (NS3 helicase)
Kim, J. L., et al (1996) Cell 87: 343-355. (NS3-4A protease structure)
Kolykhalov A. A., et al., (1997) Science 277: 570-574 (infectious RNA in chimp)

Kolykhalov A. A., et al., (2000) J. Virol. 74: 2046-2051 (enzyme inactive mutants in chimp)
Krieger, et al., (2001) J. Virol 75: 4614-4624 (adaptive)
Lai, C. L., et al. (2003) Clin. Infect. Dis. 36, 687-696.
Lamarre, D., et al. (2003) Nature 426, 186-189.
Lamarre, D., et al., (2002) Hepatology 36 (Suppl. 4) Abst. 464 (BILN 2061 discovery)
Lamarre, D., et al., (2003) Nature Medicine,
Landro, J. A., et al., (1997) Biochemistry, 36, 9340-9348. (enzyme assay)
Lin, C., and Rice, C. M. (1995) Proc. Natl. Acad. Sci. USA 92, 7622-7626 (NS3-4A in vitro assay)
Lin, C., et al. (1995) J. Virol. 69, 4373-4380 (NS4A cofactor)
Lin, C., et al. (2004) J. Biol. Chem. 279, 17508-17514
Lin, K. et al., VX-950: A Tight-Binding HCV Protease Inhibitor with a Superior Sustained Inhibitory Response in HCV Replicon Cells. Presented at the 54th Annual Meeting of the AASLD Oct. 27, 2003 Boston, Mass.
Lin, K., et al., (2003) Hepatology 38 (Suppl. 1): Abst. 137
Lohmann, V, et al., (1999) Science 285: 110-113. (replicon)
Lohmann, V., et al. (2001) J. Virol. 75, 1437-1449.
Love, R. A., et al., (1996) Cell 87: 331-342. (NS3-4A protease structure)
McCoy, M. A., et al., (2001) J. Mol. Biol. 305: 1099-1110 (NMR struture of NS3-4A protease)
McHuntchinson, J. G., et al., (1998) N. Eng. J. Med 339: 1485-1492 (pegIFN+RBV)
McHutchison, J. G., et al., (2002) Hepatology 36 (Suppl. 1), S245-252 (Hep C future therapy).
Migliaccio, G., et al. (2003) J. Biol. Chem. 278, 49164-49170.
Morrison, J. F. (1969) Biochim. Biophys. Acta 185, 269-286. (enzyme assay)
Narjes, H., et al., (2002) Hepatology 36 (Suppl. 4) Abst. 800 (BILN 2061 PK)
Neumann, A. U., et al. (1998) Science 282, 103-107
Neumann, A. U., et al., (1998) Science 285: 110-113 (HCV dynamics)
Nguyen, T. T., et al. (2003) Antimicrob. Agents Chemother. 47, 3525-3530.
Pause, A., et al., (2003) J. Biol. Chem. 278: 20374-20380. (1st PI in replicon)
Perni, B., et al., (2003) Hepatology 38 (Suppl. 1): Abst. 972
Perni, et al. (2004) Bioorg. Med. Chem. Lett. 14, in press
Perni, R. B. et al., VX-950: The Discovery of an Inhibitor of the Hepatitis C NS3•4A Protease and a Potential Hepatitis C Virus Therapeutic. Presented at the 54th Annual Meeting of the AASLD Oct. 27, 2003 Boston, Mass.
Perni, R. B., et al. (2003) Hepatology 38, Abstract 972
Pietschmann, and Bartenschlager (2001) J. Virol 75: 1252-1264.
Rice, C. M. (1996) Field Virology book, pp. 931-959
Steinkuhler, C., et al., (2001) Curr. Med. Chem. 8: 919-932 (HCV PI review)
Taliani M, et al. 1996 Anal. Biochem. 240(1):60-67. (FRET assay)
Tanji, Y., et al. (1995) J. Virol. 69, 1575-1581.
Tomei, L., et al., (1993) J. Virol. 67: 4017-4026. (NS3 serine protease)
Trozzi, C., et al., 2003, J. Virol 77: 3669-3679. (HCV resistance)
Tsantrizos, et al. (2003) Angew. Chem. Int. Ed. Engl. 42, 1356-1360
Wasley, A. & M. J. Alter (2000) Semin. Liver Dis. 20, 1-16 (HepC epidemiology)
Yan et al., (1998) Protein Sci. 7: 837-847 (NS3-4A protease structure)
Yao, N., et al. (1999) Structure Fold Des. 7, 1353-1363.

---

What is claimed is:

1. An isolated HCV polynucleotide comprising a nucleotide sequence encoding a HCV NS3/4A protease wherein a codon that corresponds to codon 156 of a wild-type polynucleotide is mutated such that it does not encode an alanine.

2. The isolated HCV polynucleotide of claim 1, wherein the codon that corresponds to codon 156 of the wild-type polynucleotide encodes an amino acid selected from the group consisting of serine, valine, and threonine.

3. The isolated HCV polynueleotide of claim 1, wherein wild-type HCV polynucleotide has the sequence of SEQ ID NO: 1.

4. A vector comprising the polynucleotide according to claim 1.

5. A host cell or cell line comprising the polynueleotide according to claim 1.

6. A host cell transformed or transfected with a vector of claim 4.

7. An isolated HCV comprising the polynucleotide according to claim 1.

8. A composition comprising the polynucleotide according to claim 1.

9. The isolated HCV polynucleotide of claim 1, where a codon that corresponds to codon 168 of the wild-type polynucleotide is mutated such that it does not encode an aspartic acid.

10. The isolated HCV polynucleotide of claim 9, wherein the codon that corresponds to codon 156 of the wild-type polynucleotide encodes a valine or a threonine and the codon that corresponds to codon 168 of the wild-type polynucleotide encodes an aspartic acid or glutamic acid.

11. The isolated HCV polynucleotide of claim 9, wherein the codon that corresponds to codon 168 of the wild-type polynucleotide encodes an amino acid selected from the group consisting of valine, alanine, glycine, and tyrosine.

12. An isolated polynucleotide comprising a nucleic acid sequence encoding SEQ ID NO: 2, wherein amino acid 156 of SEQ ID NO: 2 is mutated such that it is not an alanine.

13. An isolated polynucleotide comprising a nucleic acid sequence encoding SEQ ID NO: 2, wherein amino acid 156 of SEQ ID NO: 2 is mutated such that it is not an alanine and amino acid 168 of SEQ ID NO: 2 is mutated such that it is not an aspartic acid.

14. A vector comprising the polynucleotide according to claim 12.

15. A host cell or cell line comprising the polynucleotide according to claim 12.

16. A host cell transformed or transfected with a vector of claim 14.

17. An isolated HCV comprising the polynucleotide according to claim 12.

18. A composition comprising the polynucleotide according to claim 12.

19. A vector comprising the polynucleotide according to claim 13.

20. A host cell or cell line comprising the polynucleotide according to claim 13.

21. A host cell transformed or transfected with a vector of claim 19.

22. An isolated HCV comprising the polynucleotide according to claim 13.

23. A composition comprising the polynucleotide according to claim 13.

* * * * *